(12) United States Patent
Curro et al.

(10) Patent No.: US 8,318,284 B2
(45) Date of Patent: *Nov. 27, 2012

(54) CAPPED TUFTED LAMINATE WEB

(75) Inventors: John Joseph Curro, Cincinnati, OH (US); John Lee Hammons, Hamilton, OH (US); Jody Lynn Hoying, Maineville, OH (US); Susan Nicole Lloyd, Erlanger, KY (US); Robert Haines Turner, Cincinnati, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 192 days.

This patent is subject to a terminal disclaimer.

(21) Appl. No.: 12/817,488

(22) Filed: Jun. 17, 2010

(65) Prior Publication Data

US 2010/0255258 A1    Oct. 7, 2010

Related U.S. Application Data

(63) Continuation of application No. 12/415,140, filed on Mar. 31, 2009, now Pat. No. 8,153,226.

(51) Int. Cl.
*B32B 3/02* (2006.01)
*B32B 3/10* (2006.01)
*B32B 3/30* (2006.01)

(52) U.S. Cl. ............ 428/88; 428/92; 428/134; 428/136; 428/137; 428/138; 428/179

(58) Field of Classification Search .................... 428/88, 428/92, 161, 163, 167, 170–172, 174–176, 428/179, 182, 184, 131, 134, 136, 137, 138
See application file for complete search history.

(56) References Cited

U.S. PATENT DOCUMENTS

| 6,048,600 | A  | * | 4/2000  | Hansson ........................ 428/136 |
| 6,479,130 | B1 |   | 11/2002 | Takai et al. |
| 6,733,610 | B2 |   | 5/2004  | Mizutani et al. |
| 7,172,801 | B2 |   | 2/2007  | Hoying et al. |
| 7,410,683 | B2 |   | 8/2008  | Curro et al. |

(Continued)

FOREIGN PATENT DOCUMENTS

FR    2 713 083    6/1995

OTHER PUBLICATIONS

U.S. Appl. No. 12/470,945, filed May 22, 2009, Turner et al.

(Continued)

*Primary Examiner* — Jenna Johnson
(74) *Attorney, Agent, or Firm* — Andrew J. Hagerty

(57) ABSTRACT

A laminate web having a nonwoven web in facing relationship with a polymer film. The laminate web has a first side comprising the polymer film and a plurality of discrete tufts including fibers integral with and extending from the nonwoven web. Each of the tufts has a tuft base proximal to the nonwoven web and a distal portion opposing the tuft base. At least part of the distal portion of each of the tufts is covered by a cap, each cap being an integral extension of said polymer film extending over the distal portion of a discrete tuft. The cap has a first opening including a location of rupture in the polymer film above which the tuft extends.

5 Claims, 8 Drawing Sheets

U.S. PATENT DOCUMENTS

| | | |
|---|---|---|
| 7,507,459 B2 | 3/2009 | Turner et al. |
| 7,553,532 B2 | 6/2009 | Turner et al. |
| 2004/0122395 A1* | 6/2004 | Stone et al. .................. 604/383 |
| 2004/0229008 A1 | 11/2004 | Hoying |
| 2005/0281976 A1 | 12/2005 | Curro et al. |
| 2006/0019056 A1* | 1/2006 | Turner et al. .................. 428/85 |
| 2006/0286343 A1 | 12/2006 | Curro et al. |
| 2007/0116926 A1 | 5/2007 | Hoying et al. |
| 2008/0119807 A1 | 5/2008 | Curro et al. |
| 2008/0154226 A9 | 6/2008 | Hammons |
| 2009/0157030 A1 | 6/2009 | Turner et al. |

OTHER PUBLICATIONS

Office Action for U.S. Appl. No. 12/415,140 dated Mar. 2, 2011; Curro, et al.; filed Mar. 31, 2009.

Office Action for U.S. Appl. No. 12/415,140 dated Oct. 7, 2010; Curro, et al.; filed Mar. 31, 2009.

Office Action for U.S. Appl. No. 12/558,693 dated Mar. 17, 2011; Turner, et al.; filed Sep. 14, 2009.

Office Action for U.S. Appl. No. 12/558,693 dated Oct. 8, 2010; Turner, et al.; filed Sep. 14, 2009.

* cited by examiner

CAPPED TUFTED LAMINATE WEB

CROSS REFERENCE TO RELATED APPLICATION

This application is a continuation of U.S. application Ser. No. 12/415,140 filed Mar. 31, 2009 now U.S. Pat. No. 8,153,226.

FIELD OF THE INVENTION

The disclosure herein relates generally to a capped tufted laminate web and an article incorporating a capped tufted laminate web.

BACKGROUND OF THE INVENTION

Laminates of webs, such as films and fibrous webs are known in the art. For example, nonwoven webs are often laminated with polymer films such that they are useful as materials in disposable products such as backsheets on disposable absorbent diapers. In such laminates the nonwoven portion can provide softness while the film portion can provide for fluid impermeability.

Laminates in which nonwoven fibers protrude through a polymer film can be useful for providing an absorbent structure in which the nonwoven acts as the conveyor of fluid from one side of the polymer film to the other. The laminate can be structured such that the fluid collecting side of the laminate is the polymer film and nonwoven fibers protrude through the polymer film to the fluid collecting side of the laminate. For example, in a sanitary napkin or diaper, such a laminate can be practical for use as a topsheet that transports fluid from the body facing surface of the sanitary napkin more deeply into the sanitary napkin towards the absorbent core. If the fibers are structured as tufts in which the fibers comprising the tuft generally converge near the base of the tuft, the convergence of fibers can provide for small capillaries that can aid in transporting the fluid through the topsheet. Further, the fibers protruding through the polymer film can have a pleasant tactile impression.

Depending on the arrangement of the fibers of the nonwoven protruding through the polymer film and the fluid acquired by the tufts, the fibers on the fluid collecting side of the film may retain some fluid in small capillaries that might exist between the fibers. If the laminate is an absorbent article, such a sanitary napkin, diaper, or tampon, this may result in the retained fluid appearing as a stain on the body facing surface of the laminate. Stains of menses, vaginal discharge, urine, and feces may not be viewed favorably by the wearer of the absorbent article. If the laminate is used in a wipe or cleaning device, the retained fluid may be visually perceptible to the user of the device and the user may misinterpret the staining as an indication that the utility of the wipe or cleaning device is exhausted even when such a determination is in reality premature.

With this limitation in mind, there is a continuing unaddressed need for a laminate of a polymer film and fibrous web in which the fibrous web protrudes through the polymer film that has improved capabilities for masking fluid retained in the fibers protruding through the polymer film.

SUMMARY OF THE INVENTION

Disclosed herein is a laminate web comprising a nonwoven web in facing relationship with a polymer film, the laminate web comprising a first side comprising the polymer film and a plurality of discrete tufts comprising fibers integral with and extending from the nonwoven web, wherein each of the tufts has a tuft base proximal to the nonwoven web and a distal portion opposing the tuft base, wherein at least part of the distal portion of each of the tufts is covered by a cap, each cap being an integral extension of the polymer film extending over the distal portion of a discrete tuft, the cap comprising a first opening comprising a location of rupture in the polymer film above which the tuft extends.

Disclosed herein is an absorbent article comprising a topsheet in facing relationship with an absorbent core, the topsheet comprising a laminate web comprising a first side comprising the polymer film and a plurality of discrete tufts comprising fibers integral with and extending from the nonwoven web, wherein the nonwoven web is between the polymer film and the absorbent core, wherein each of the tufts has a tuft base proximal to the nonwoven web and a distal portion opposing the tuft base, wherein at least part of the distal portion of each of the tufts is covered by a cap, each cap being an integral extension of the polymer film extending over the distal portion of a discrete the tuft, the cap having a first opening comprising a location of rupture in the polymer film above which the tuft extends.

DETAILED DESCRIPTION OF THE INVENTION

Figure 1:
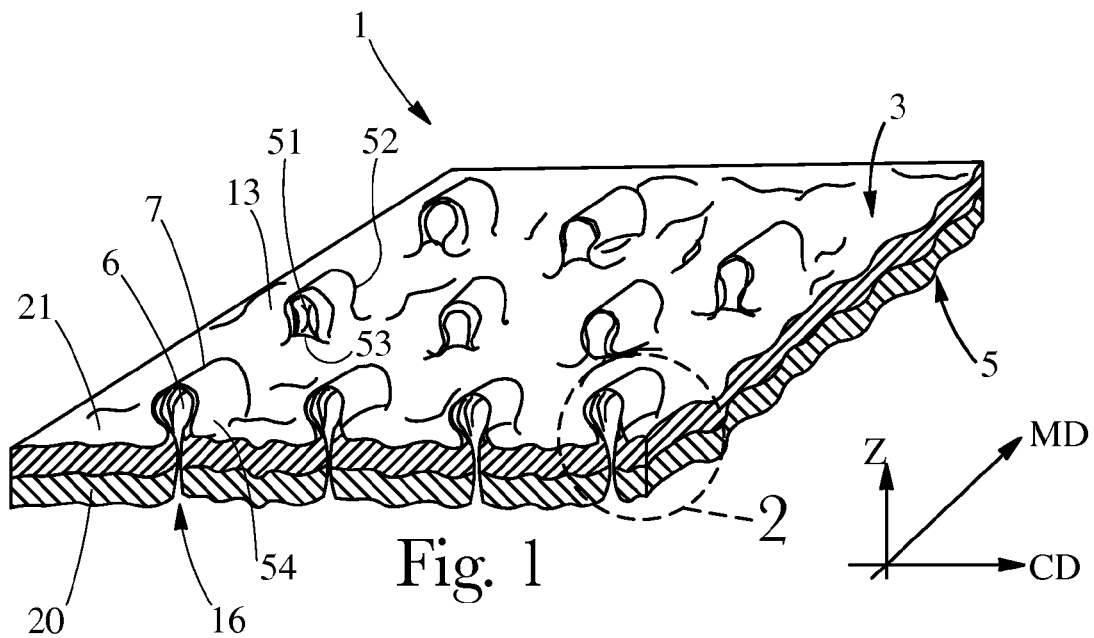
FIG. 1 is a perspective view of a web of the present invention.

FIG. 1 shows a laminate web 1 of the present invention, hereinafter referred to simply as web 1. Web 1 comprises at least two layers. The layers are referred to herein as generally planar, two-dimensional precursor webs, such as first precursor web 20 and second precursor web 21. First precursor web 20 is a fibrous nonwoven web and second precursor web 21 is a polymer film. Precursor webs 20 and 21 (and any additional webs) can be joined by adhesive, thermal bonding, ultrasonic bonding and the like. As disclosed below, the constituent precursor webs of web 1 can be joined by interlocking mechanical engagement resulting from the formation of tufts 6. A representative tuft 6 for the embodiment of web 1 shown in FIG. 1 is shown in a further enlarged view in FIG. 2. A tuft can be a plurality of raised loops of fibers or a pile of fibers integral with and out of plane of the web from which the loops or pile extend.

Web 1 has a first side 3 and a second side 5, the term "sides" being used in the common usage of generally planar two-dimensional webs, such as paper and films that have two sides when in a generally flat condition. Each precursor web 20 and 21 has a first surface 12 and 13, respectively, and a second surface 14 and 15, respectively (shown in FIG. 3). The first surfaces 12 and 13 can be body facing surfaces and the second surfaces 14 and 15 can be garment facing surfaces. Web 1 has a machine direction (MD) and a cross machine direction (CD) as is commonly known in the art of web manufacture. First precursor web 20 can be a nonwoven web comprised of substantially randomly oriented fibers. By "substantially randomly oriented" is meant that, due to processing conditions of the precursor web, there may be a higher amount of fibers oriented in the MD than the CD, or vice-versa. For example, in spunbonding and meltblowing processes continuous strands of fibers are deposited on a support moving in the MD. Despite attempts to make the orientation of the fibers of the spunbond or meltblown nonwoven web truly "random," usually a slightly higher percentage of fibers are oriented in the MD as opposed to the CD. Second precursor web 21 can be a polymer film or an apertured polymer film, such as a polyethylene film.

Figure 3:
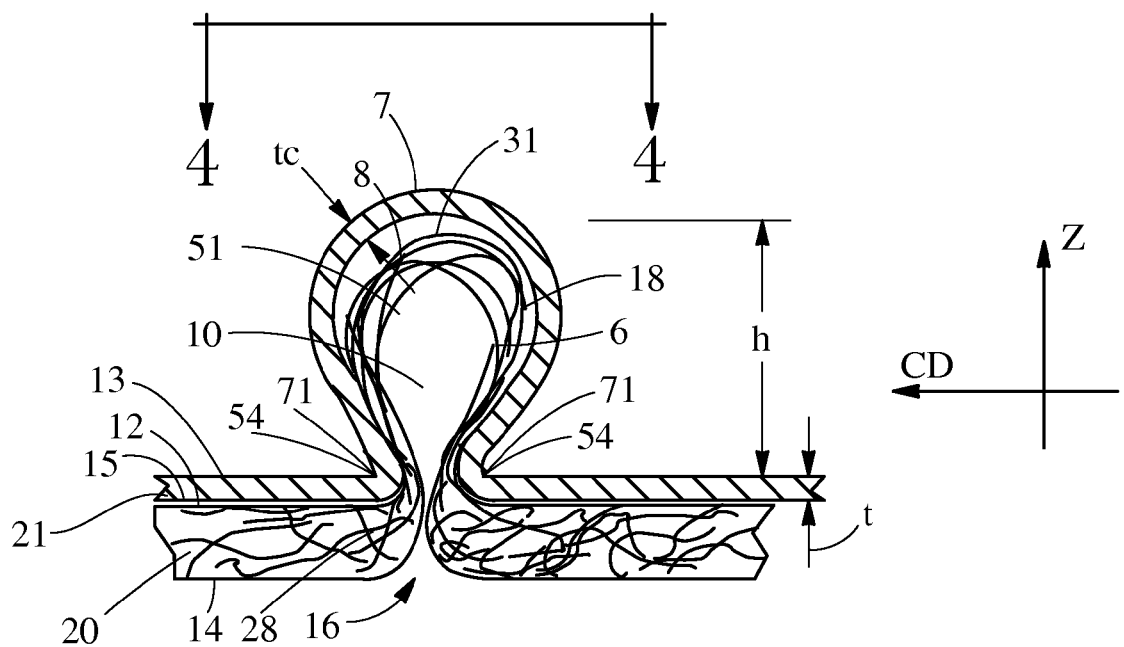
FIG. 3 is a cross-sectional view of section 3-3 of FIG. 2.

In one embodiment, first side 3 of web 1 is defined by exposed portions of the first surface 13 of second precursor web 21 and at least one, but preferably a plurality of, discrete tufts 6 which are integral extensions of the fibers of a nonwoven first precursor web 20. As shown in FIG. 3, each tuft 6 can comprise a plurality of looped, aligned fibers 8 extending through the first surface 13 of second precursor web 21 and outwardly from the first surface 13 thereof. In another embodiment each tuft 6 can comprise a plurality of non-looped fibers 18 (as shown in FIG. 3) that extend outwardly from the first surface 13.

As used herein, the term "nonwoven web" refers to a web having a structure of individual fibers or threads which are interlaid, but not in a repeating pattern as in a woven or knitted fabric, which do not typically have randomly oriented fibers. Nonwoven webs or fabrics have been formed from many processes, such as, for example, meltblowing processes, spunbonding processes, hydroentangling, airlaying, and bonded carded web processes, including carded thermal bonding. The basis weight of nonwoven fabrics is usually expressed in grams per square meter (gsm). The basis weight of the laminate web is the combined basis weight of the constituent layers and any other added components. Fiber diameters are usually expressed in microns; fiber size can also be expressed in denier, which is a unit of weight per length of fiber. The basis weight of laminate webs suitable for use in the present invention can range from 10 gsm to 500 gsm, depending on the ultimate use of the web 1.

The constituent fibers of nonwoven precursor web 20 can be comprised of polymers such as polyethylene, polypropylene, polyester, and blends thereof. The fibers can comprise cellulose, rayon, cotton, or other natural materials or blends of polymer and natural materials. The fibers can also comprise a super absorbent material such as polyacrylate or any combination of suitable materials. The fibers can be mono-component, bicomponent, and/or biconstituent, non-round (e.g., capillary channel fibers), and can have major cross-sectional dimensions (e.g., diameter for round fibers) ranging from 0.1-500 microns. For example, one type of fibers suitable for the nonwoven web includes nanofibers. Nanofibers are described as fibers having a mean diameter of less than 1 micron. Nanofibers can comprise all of the fibers in a nonwoven web or a portion of the fibers in a nonwoven web. The constituent fibers of the nonwoven precursor web may also be a mixture of different fiber types, differing in such features as chemistry (e.g. polyethylene and polypropylene), components (mono- and bi-), denier (micro denier and >20 denier), shape (i.e. capillary and round) and the like. The constituent fibers can range from about 0.1 denier to about 100 denier.

As used herein, "spunbond fibers" refers to small diameter fibers which are formed by extruding molten thermoplastic material as filaments from a plurality of fine, usually circular capillaries of a spinneret with the diameter of the extruded filaments then being rapidly reduced. Spunbond fibers are generally not tacky when they are deposited on a collecting surface. Spunbond fibers are generally continuous and have average diameters (from a sample of at least 10) larger than 7 microns, and more particularly, between about 10 and 40 microns.

As used herein, the term "meltblowing" refers to a process in which fibers are formed by extruding a molten thermoplastic material through a plurality of fine, usually circular, die capillaries as molten threads or filaments into converging high velocity, usually heated, gas (for example air) streams which attenuate the filaments of molten thermoplastic material to reduce their diameter, which may be to microfiber diameter. Thereafter, the meltblown fibers are carried by the high velocity gas stream and are deposited on a collecting surface, often while still tacky, to form a web of randomly dispersed meltblown fibers. Meltblown fibers are microfibers which may be continuous or discontinuous and are generally smaller than 10 microns in average diameter.

As used herein, the term "polymer" generally includes, but is not limited to, homopolymers, copolymers, such as for example, block, graft, random and alternating copolymers, terpolymers, etc., and blends and modifications thereof. In addition, unless otherwise specifically limited, the term "polymer" includes all possible geometric configurations of the material. The configurations include, but are not limited to, isotactic, atactic, syndiotactic, and random symmetries.

As used herein, the term "monocomponent" fiber refers to a fiber formed from one or more extruders using only one polymer. This is not meant to exclude fibers formed from one polymer to which small amounts of additives have been added for coloration, antistatic properties, lubrication, hydrophilicity, etc. These additives, for example titanium dioxide for coloration, are generally present in an amount less than about 5 weight percent and more typically about 2 weight percent.

As used herein, the term "bicomponent fibers" refers to fibers which have been formed from at least two different polymers extruded from separate extruders but spun together to form one fiber. Bicomponent fibers are also sometimes referred to as conjugate fibers or multicomponent fibers. The polymers are arranged in substantially constantly positioned distinct zones across the cross-section of the bicomponent fibers and extend continuously along the length of the bicomponent fibers. The configuration of such a bicomponent fiber may be, for example, a sheath/core arrangement wherein one polymer is surrounded by another, or may be a side-by-side arrangement, a pie arrangement, or an "islands-in-the-sea" arrangement.

As used herein, the term "biconstituent fibers" refers to fibers which have been formed from at least two polymers extruded from the same extruder as a blend. Biconstituent fibers do not have the various polymer components arranged in relatively constantly positioned distinct zones across the cross-sectional area of the fiber and the various polymers are usually not continuous along the entire length of the fiber, instead usually forming fibrils which start and end at random. Biconstituent fibers are sometimes also referred to as multiconstituent fibers.

As used herein, the term "non-round fibers" describes fibers having a non-round cross-section, and includes "shaped fibers" and "capillary channel fibers." Such fibers can be solid or hollow, and they can be tri-lobal, delta-shaped, and are preferably fibers having capillary channels on their outer surfaces. The capillary channels can be of various cross-sectional shapes such as "U-shaped", "H-shaped", "C-shaped" and "V-shaped". One practical capillary channel fiber is T-401, designated as 4DG fiber available from Fiber Innovation Technologies, Johnson City, Tenn. T-401 fiber is a polyethylene terephthalate (PET polyester).

As used herein, the term "integral" as in "integral extension" when used for the tufts 6 refers to fibers of the tufts 6 having originated from the fibers of the first precursor web 20. Therefore, the looped fibers 8 and non-looped fibers 18 of tufts 6, can be plastically deformed and extended fibers of the first precursor web 20, and are, therefore, integral with first precursor web 20. As used herein, "integral" is to be distinguished from fibers introduced to or added to a separate precursor web for the purpose of making tufts, as is commonly done in conventional carpet making, for example.

As used herein, the term "integral" as in "integral extension" when used for the cap 7 refers to the substrate forming the cap 7 having originated from the polymer film that is the second precursor web 21. Therefore, the cap 7 can be a plastically deformed extended substrate of the second precursor web 21, and is, therefore, integral with the second precursor web 21. As used herein, "integral" is to be distinguished from a substrate introduced to or added to a separate precursor web for the purpose of making a cap 7.

As used herein, the term "opacity" refers to the property of a substrate or printed substrate which measures the capacity of the substrate to hide or obscure from view an object placed behind the substrate relative to the point from which observation is made. Opacity can be reported as the ratio, in percent, of the diffuse reflectance of a substrate backed by a black body having a reflectance of 0.5% to the diffuse reflectance of the same substrate backed with a white body having an absolute reflectance of 89%. Opacity can be measured as described in ASTM D 589-97, Standard Test Method for Opacity of Paper (15°/Diffuse Illuminant A, 89% Reflectance Backing and Paper Backing).

A substrate high in opacity will not permit much, if any, light to pass through the substrate. A substrate having low opacity will permit much, if not nearly all, light to pass through the substrate. Opacity can range from 0 to 100%. As used herein, the term "low opacity" refers to a substrate or printed substrate having opacity less than 50%. As used herein, the term "high opacity" refers to a substrate or printed substrate having opacity greater than or equal to 50%. As used herein, the term "opaque" refers to a substrate or printed substrate that has an opacity greater than or equal to 50%.

As used herein, the term "adjacent" means not distant and implies an absence of anything of the same kind in between the structures that are adjacent.

The number, spacing, and dimensions of tufts 6 can be varied to give varying texture to first side 3 of web 1. For example, if tufts 6 are sufficiently closely spaced the first side 3 of web 1 can have a terry cloth-like feel. Alternatively, tufts 6 can be arranged in patterns such as lines or filled shapes to create portions of a laminate web having greater texture, softness, bulk, absorbency or visual design appeal. For example, when tufts 6 are arranged in a pattern of a line or lines, the tufts can have the appearance of stitching. Likewise, the size dimensions, such as the height, length and width of individual tufts 6 can be varied. Single tufts can be as long as about 3 cm in length and can be made alone or dispersed among tufts of various sizes.

First precursor web 20 can be a fibrous woven or nonwoven web comprising fibers having sufficient elongation properties to have portions formed into tufts, as described more fully below. Tufts are formed by urging fibers out-of-plane in the Z-direction at discrete, localized, portions of first precursor web 20. The urging out-of-plane can be due to fiber displacement, i.e., the fiber is able to move relative to other fibers and be "pulled," so to speak, out-of-plane. More often, however, for most nonwoven first precursor webs 20, the urging out-of-plane is due to the fibers of tufts 6 having been at least partially plastically stretched and permanently deformed to form tufts 6. Therefore, in one embodiment, depending on the desired height of tufts 6, the constituent fibers of a nonwoven first precursor webs 20 can exhibit an elongation to break of at least about 5%, of at least about 10%, of at least about 25%, of at least about 50%, or of at least about 100%. Elongation to break can be determined by simple tensile testing, such as by use of Instron tensile testing equipment, and can generally be found on material data sheets from suppliers of such fibers or webs.

It can be appreciated that a suitable nonwoven first precursor web 20 should comprise fibers capable of experiencing sufficient plastic deformation and tensile elongation, or are capable of sufficient fiber mobility, such that looped fibers 8 are formed. However, it is recognized that a certain percentage of fibers urged out of the plane of the first surface 12 of first precursor web 20 will not form a loop, but instead will break and form loose ends. Such fibers are referred to herein as "loose" fibers or non-looped fibers (i.e. loose fiber ends) 18 as shown in FIG. 3. Non-looped fibers 18 are not necessarily undesirable for the present invention, and in some embodiments, most or all of the fibers of tufts 6 can be non-looped fibers 18. Non-looped fibers 18 can also be the result of forming tufts 6 from nonwoven webs consisting of, or containing, cut staple fibers. In such a case, some number of the staple fiber ends may protrude into the tuft 6, depending upon such things as the number of staple fibers in the web, the staple fiber cut length, and the height of the tufts. In some instances, it may be desired to use a blend of fibers of different lengths in a precursor web or fibers of different lengths in different layers.

This may be able to selectively separate the longer fibers from the shorter fibers. The longer fibers may predominately form the tuft 6 while the shorter fibers predominately remain in the portion of the web not forming the tuft 6. A mixture of fiber lengths can include fibers of approximately 2 to 8 centimeters for the longer fibers and less than about 1 centimeter for the shorter fibers.

First precursor web 20 can be a fibrous woven or nonwoven web comprising elastic or elastomeric fibers. Elastic or elastomeric fibers can be stretched at least about 50% and return to within 10% of their original dimension. Tufts 6 can be formed from elastic fibers if the fibers are simply displaced due to the mobility of the fiber within the nonwoven, or if the fibers are stretched beyond their elastic limit and are plastically deformed.

Second precursor web 21 can be a polymer film web have sufficient integrity to be formed into the laminate by the process described below, and that it have sufficiently less elongation properties relative to first precursor web 20, such that upon experiencing the strain of fibers from first precursor web 20 being urged out-of-plane in the direction of second precursor web 21, second precursor web 21 will rupture, e.g., by tearing due to extensional failure, such that portions of first precursor web 20 can extend through, (i.e., "punch through" so to speak), the plane of the first surface 13 of second precursor web 21 to form tufts 6 on first side 3 of web 1 and a cap 7 will remain over the distal portion 31 of each tuft 6.

The second precursor web 21 can be microtextured polymer film. By microtextured it is meant that there are a plurality of microfeatures in the second precursor web 21 between the tufts 6, such microfeatures being sized and dimensioned so that a plurality of microfeatures can fit between adjacent tufts 6. That is, the micro features are sized and dimensioned such that the microfeatures can have a maximum dimension smaller than one-half the distance between adjacent tufts 6. The microfeatures can, for example, be microapertures or micro bubbles, examples of which are disclosed in U.S. Pat. No. 7,402,732, issued to Stone et al. and U.S. Pat. No. 4,839,216 issued to Curro et al., U.S. Pat. No. 4,609,518 issued to Curro et al., and U.S. Pat. No. 4,609,518 issued to Curro et al. The polymer film can be an apertured polymer film, the apertures of which each have an area of between about 0.01 mm$^2$ and about 0.78 mm$^2$. The microfeatures can be raised portions. Raised portions can be integral extensions of the polymer film or can be materials added to the surface of the polymer film.

Figure 2:
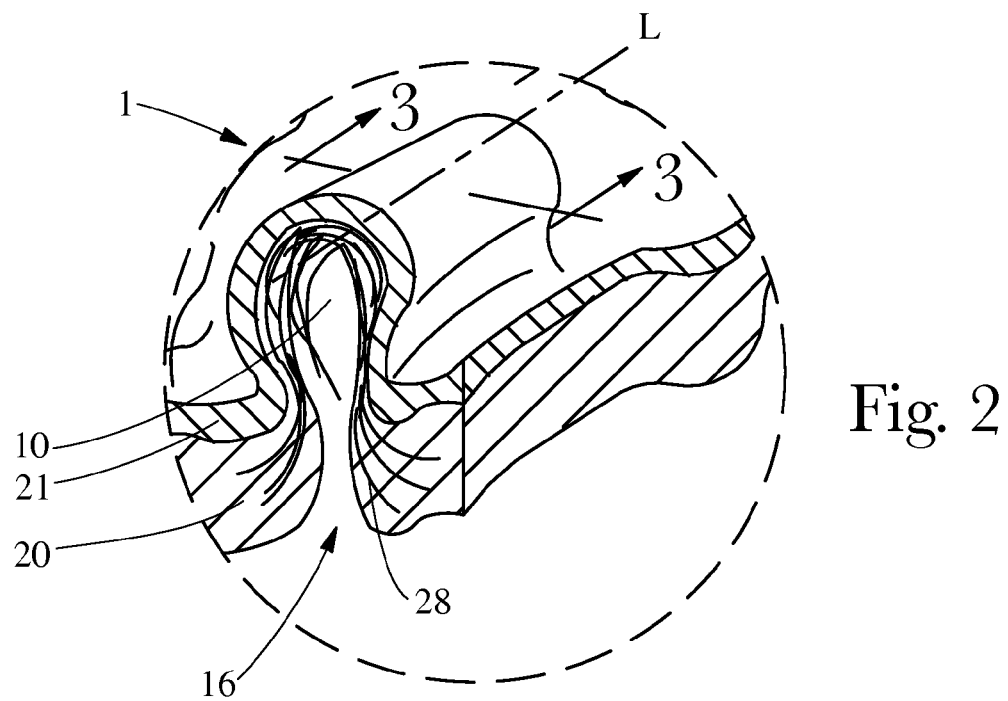
FIG. 2 is an enlarged view of a portion of the web shown in FIG. 1.

As shown in FIG. 2 or 3, tuft 6 can comprise a plurality of looped fibers 8 that are substantially aligned such that tuft 6 has a distinct linear orientation and a longitudinal axis L. Tuft 6 can also have a transverse axis T generally orthogonal to longitudinal axis L in the MD-CD plane. In the embodiment shown in FIGS. 1 and 2, longitudinal axis L is parallel to the MD. In one embodiment, the spaced apart tufts 6 have generally parallel longitudinal axes L. The number of tufts 6 per unit area of web 1, i.e., the area density of tufts 6, can be varied from 1 tuft per unit area, e.g., square centimeter to as high as 100 tufts per square centimeter. There can be at least 10, or at least 20 tufts 6 per square centimeter, depending on the end use. In general, the area density need not be uniform across the entire area of web 1, but tufts 6 can be only in certain regions of web 1, such as in regions having predetermined shapes, such as lines, stripes, bands, circles, and the like. Tufts 6 can be spaced sufficiently closely so as to effectively cover first side 3 of web 1.

As can be appreciated by the description herein, in many embodiments of web 1 openings 4 of second precursor web 21 can have a distinct linear orientation and a longitudinal axis, which is oriented parallel to the longitudinal axis L of its corresponding tuft 6. Likewise, openings 4 will also have a transverse axis generally orthogonal to longitudinal axis in the MD-CD plane.

As shown in FIGS. 1-4, tufts 6 extend above openings 4 in second precursor web 21. Openings 4 are formed by locally rupturing second precursor web 21 by the process described in detail below. Rupture may involve a simple splitting open of second precursor web 21 such that a portion or portions of second precursor web 21 can be deflected or urged out-of-plane (i.e., the plane of second precursor web 21) to form cap structures, referred to herein as cap, or caps, 7. The form and structure of caps 7 may be dependent upon the material properties of second precursor web 21. Caps 7 can have the general structure of one or more caps 7, as shown in FIGS. 1 and 2.

Tufts 6 are, in a sense, "punched above" second precursor web 21 and can be "locked" in place by frictional engagement with openings 4. In some embodiments, for example, the lateral width of opening 4 (i.e., the dimension measured parallel to its transverse axis) can be less than the maximum width of the tooth that formed the opening (per the process described below). This indicates a certain amount of recovery at the opening that tends to constrain tuft 6 from pulling back out through opening 4. The frictional engagement of the tufts and openings provides for a laminate web structure having permanent tufting on one side that can be formed without adhesives or thermal bonding.

As shown in FIGS. 1-4, one characteristic of tufts 6 can be the predominant directional alignment of the fibers 8 or 18. For example, looped, aligned fibers 8 can be described as having a significant or major vector component parallel to the Z-CD plane and the looped fibers 8 have a substantially uniform alignment with respect to transverse axis T when viewed in plan view, such as in FIGS. 4. By "looped" fibers 8 is meant fibers 8 that are integral with and begin and end in first precursor web 20 but extend outwardly in the Z-direction from first surface 13 of second precursor web 21. By "aligned" with respect to looped fibers 8 of tufts 6 is meant that looped fibers 8 are all generally oriented such that, if viewed in plan view as in FIG. 4, each of the looped fibers 8 has a significant vector component parallel to the transverse axis T, and can have a major vector component parallel to the transverse axis T.

In contrast, non-looped fibers 18 are integral with, but only begin in first precursor web 20 and have a free end extending outwardly in the Z-direction from first surface 13 of second precursor web 21. Non-looped fibers 18 can also have a generally uniform alignment described as having a significant or major vector component parallel to the Z-CD plane.

For both looped fibers 8 and non-looped fibers 18, the alignment can be a characteristic of tufts 6 prior to any post-manufacture deformation due to winding onto a roll, or compression in use in an article of manufacture.

Figure 4:
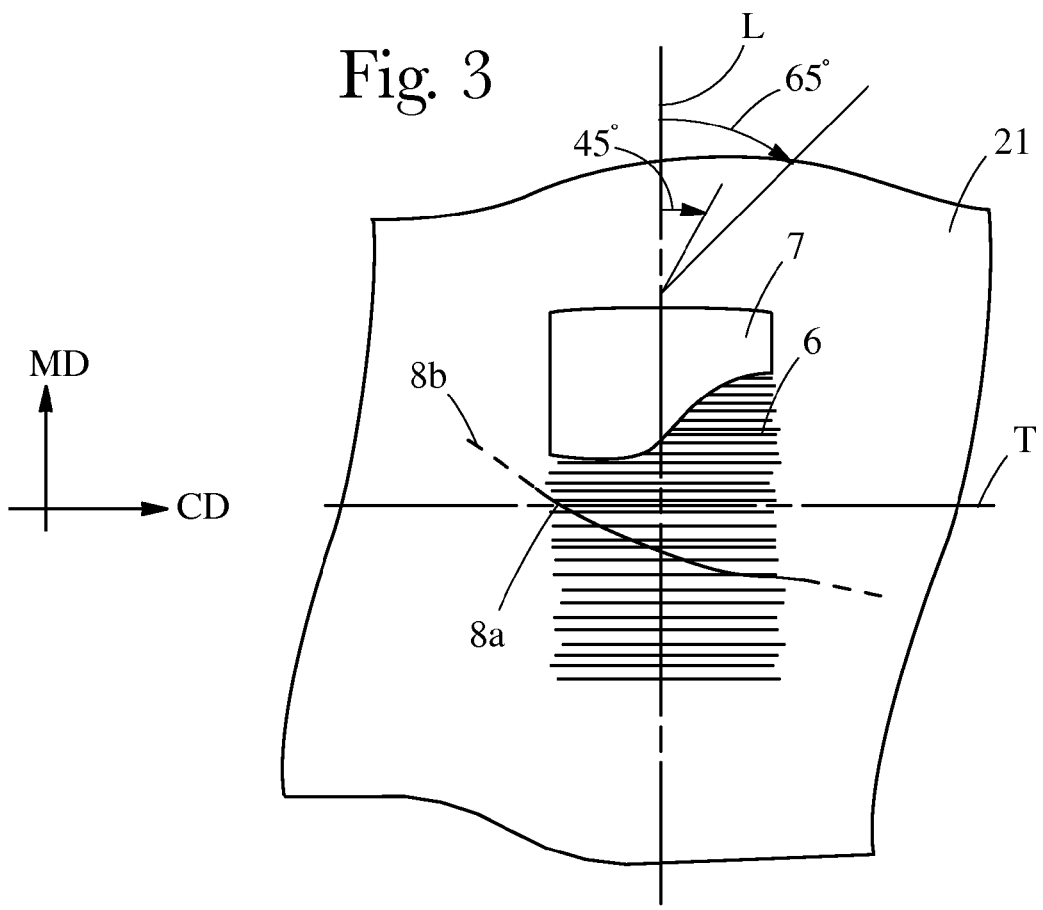
FIG. 4 is a cutaway plan view of a portion of the web as indicated by 4-4 in FIG. 3.

As used herein, a looped fiber 8 oriented at an angle of greater than 45 degrees from the longitudinal axis L when viewed in plan view, as in FIG. 4, has a significant vector component parallel to the transverse axis T. As used herein, a looped fiber 8 oriented at an angle of greater than 60 degrees from longitudinal axis L when viewed in plan view, as in FIG. 4, has a major vector component parallel to the transverse axis T. In some embodiments, at least 50%, at least 70%, and at least 90% of fibers 8 of tuft 6 have a significant or a major vector component parallel to transverse axis T. Fiber orientation can be determined by use of magnifying means if necessary, such as a microscope fitted with a suitable measurement scale. In general, for a non-linear segment of fiber viewed in plan view, a straight-line approximation for both longitudinal axis L and the looped fibers 8 can be used for determining the angle of looped fibers 8 from longitudinal axis L. For example, as shown in FIG. 4, one fiber 8a is shown emphasized by a heavy line, and its linear approximation 8b is shown as a dashed line. This fiber makes an angle of approximately 80 degrees with the longitudinal axis (measured counterclockwise from L).

The orientation of looped fibers 8 in the tufts 6 is to be contrasted with the fiber composition and orientation for first precursor web 20, which, for nonwoven webs can be described as having a substantially randomly-oriented fiber alignment.

In the embodiment shown in FIG. 1 the longitudinal axes L of tufts 6 are generally aligned in the MD. Tufts 6 and, therefore, longitudinal axes L, can, in principle, be aligned in any orientation with respect to the MD or CD. Therefore, in general, it can be said that for each tuft 6, the looped aligned fibers 8 are aligned generally orthogonal to the longitudinal axis L such that they have a significant vector component parallel to transverse axis T, and can have a major vector component parallel to transverse axis T.

In some embodiments, as described below, another characteristic of tufts 6 comprising predominantly looped, aligned fibers 8, can be their generally open structure characterized by open void area 10 defined interiorly of tufts 6, as shown in FIGS. 2 and 3. The void area 10 may have a shape that is wider or larger at the distal portion 31 of the tuft 6 and narrower at the tuft base 17 of the tuft 6. This is opposite to the shape of the tooth which is used to form the tuft 6. By "void area" is not meant an area completely free of any fibers; the term is meant as a general description of the general appearance of tufts 6. Therefore, it may be that in some tufts 6 a non-looped fiber 18 or a plurality of loose non-looped fibers 18 may be present in the void area 10. By "open" void area is meant that the two longitudinal ends of tuft 6 are generally open and free of fibers, such that tuft 6 can form something like a "tunnel" structure in an uncompressed state, as shown in FIG. 3.

Additionally, as a consequence of a method of making web 1, the second side 5 of web 1 exhibits discontinuities 16 characterized by a generally linear indentation defined by formerly random fibers of the second surface 14 of first precursor web 20 having been urged directionally (i.e., in the "Z-direction" generally orthogonal to the MD-CD plane as shown in FIGS. 1 and 3) into tufts 6 by the teeth of the forming structure, described in detail below. The abrupt change of orientation exhibited by the previously randomly-oriented fibers of first precursor web 20 defines the discontinuity 16, which exhibits a linearity such that it can be described as having a longitudinal axis generally parallel to longitudinal axis L of the tuft 6. Due to the nature of many nonwoven webs useful as first precursor webs 20, discontinuity 16 may not be as distinctly noticeable as tufts 6. For this reason, the discontinuities 16 on the second side 5 of web 1 can go unnoticed and may be generally undetected unless web 1 is closely inspected. As such, the second side 5 of web 1 can have the look and feel of an un-tufted first precursor web 20. Thus in some embodiments, web 1 can have the textured look and feel of terry cloth on first side 3, and a relatively smooth, soft look and feel on second side 5. In other embodiments, discontinuities 16 can appear as apertures, and may be apertures through web 1 via the ends of the tunnel-like tufts 6.

From the description of web 1 comprising a nonwoven first precursor web 20, it can be seen that the fibers 8 or 18 of tuft 6 can originate and extend from either the first surface 12 or the second surface 14 of first precursor web 20. Of course the fibers 8 or 18 of tuft 6 can also extend from the interior 28 of first precursor web 20. As shown in FIG. 3, the fibers 8 or 18 of tufts 6 extend due to having been urged out of the generally two-dimensional plane of first precursor web 20 (i.e., urged in the "Z-direction" as shown in FIG. 3). In general, the fibers 8 or 18 of the tufts 6 comprise fibers that are integral with and extend from the fibers of the first precursor web 20.

Therefore, from the above description, it is understood that in one embodiment web 1 can be described as being as a laminate web comprising a nonwoven web in facing relationship with a polymer film, the laminate web comprising a first side comprising the polymer film and a plurality of discrete tufts comprising fibers integral with and extending from the nonwoven web, wherein each of the tufts has a tuft base proximal to the nonwoven web and a distal portion opposing the tuft base, wherein at least part of the distal portion of each of the tufts is covered by a cap, each cap being an integral extension of the polymer film extending over the distal portion of a discrete tuft, the cap comprising a first opening comprising a location of rupture in the polymer film above which the tuft extends.

The extension of fibers 8 or 18 can be accompanied by a general reduction in fiber cross sectional dimension (e.g., diameter for round fibers) due to plastic deformation of the fibers and Poisson's ratio effects. Therefore, the aligned looped fibers 8 of tuft 6 can have a tuft average fiber diameter less than the nonwoven web average fiber diameter of the fibers of first precursor web 20. That is, portions of the fibers comprising the tufts 6 can have a fiber diameter less than the nonwoven web fiber diameter. It is believed that this reduction in fiber diameter contributes to the perceived softness of the first side 3 of web 1, a softness that can be comparable to cotton terry cloth, depending on the material properties of the first precursor web 20. It has been found that the reduction in fiber cross-sectional dimension is greatest intermediate the tuft base 17 and the distal portion 31 of tuft 6. This is believed to be due to the method of making, as disclosed below. As shown on FIG. 3, it is believed that portions of fibers at the tuft base 17 and distal portion 31 of tufts 6 are adjacent the tip of teeth 110 of roll 104, described more fully below, and are frictionally locked and immobile during processing. Thus, the intermediate portions of tufts 6 are more free to stretch, or elongate, and accordingly, can experience a corresponding fiber cross sectional dimension reduction. The first precursor web 20 may laterally squeeze the tuft base 17 of the tuft 6. The tuft base 17 of the tuft 6 may even be closed (if the fibers from the tuft 6 are close enough together to touch) or may remain open. Generally, any opening at the tuft base 17 is narrow. The closing or narrowing or squeezing of other fibers at the tuft base 17 can help to stabilize the tufts 6.

Caps 7 are integral extensions of the second precursor web 21, which is a polymer film. At least part of a distal portion 31 of each of the tufts 6 is covered by a cap 7. As shown in FIGS. 1-4, a cap 7 can be a tunnel shaped cap 7 having a first opening 51 and a second opening 52. The first opening 51 comprises a location of rupture 53 in the second precursor web and the tuft 6 extends above the location of rupture 53. The caps 7 integrally extend from the second precursor web 21 proximal the location of rupture 53. The location of rupture 53 may be a point or a line. A cap 7 is formed by rupturing the second precursor web 21 at least one location of rupture 53 and stretching the polymer film out of plane of the first surface 13 of the second precursor web 21 to form an opening such as first opening 51 or a first opening 51 and a second opening 52. The location of rupture 53 can define at least part of the boundary of the opening 4. The remainder of the opening 4 can be defined by one or more additional locations of rupture or portions of the cap 7 proximal the location from which the cap 7 integrally extends from the second precursor web 21. The second precursor web 21 can be fluid impervious in absence of a rupture 53.

The first opening 51 can be arch shaped such that the first opening 51 is broadest proximal the first surface 13 of the second precursor web 21 and generally becomes narrower towards the portion of the cap covering the distal portion 31 of the tuft 6. The cap 7 can have a cap base 71 proximal the first surface 13 of the second precursor web 21. The cap base 71 can be narrower than a portion of the cap 7 away from the cap base 71. That is, the distance between the extension locations 54 can be less than maximum lateral extent of the cap 7 away (i.e. above) from the cap base 71. The first opening 51 can be uppercase omega shaped (Ω) such the first opening 51 is narrower proximal the first surface 13 of the second precursor web 21 than at a location midway between the tuft base 17 and the distal portion 31 of tuft 6. Similarly, if a second opening 52 is present, second opening 52 can be arch shaped such that the second opening 52 is broadest proximal the first surface 13 of the second precursor web 21 and generally narrows towards the portion of the cap 7 covering the distal portion 31 of the tuft 6. The second opening 52 can be uppercase omega shaped (Ω) such that the second opening 52 is narrower proximal the first surface 13 of the second precursor web 21 than at a location midway between the tuft base 17 and the distal portion 31 of tuft 6. The second opening 52 can oppose the first opening 51 in that at least part of the tuft 6 is between second opening 52 and first opening 51. The first opening 51, the second opening 52, and any additional openings can make the laminate web 1 liquid pervious.

If there is a first opening 51 and a second opening 52, the cap 7 can integrally extend from the second precursor web 21 at least two extension locations 54 spaced apart from one another by the first opening 51 and second opening 52. The at least two extension locations 54 can be at opposing positions on opposing sides of the tuft 6. The cap 7 can integrally extend from the second precursor web 21 (polymer film) at least two extension locations 54, each extension location 54 adjacent a location of rupture 53. In addition to a first opening 51 and a second opening 52, there can be additional openings. For instance, if there are three or more openings (e.g., first opening 51, second opening 52, and third opening), the cap 7 can integrally extend from the second precursor web 21 at least three extension locations 54 spaced apart from one another by the openings (e.g. first opening 51, second opening 52, and third opening).

Figure 5:
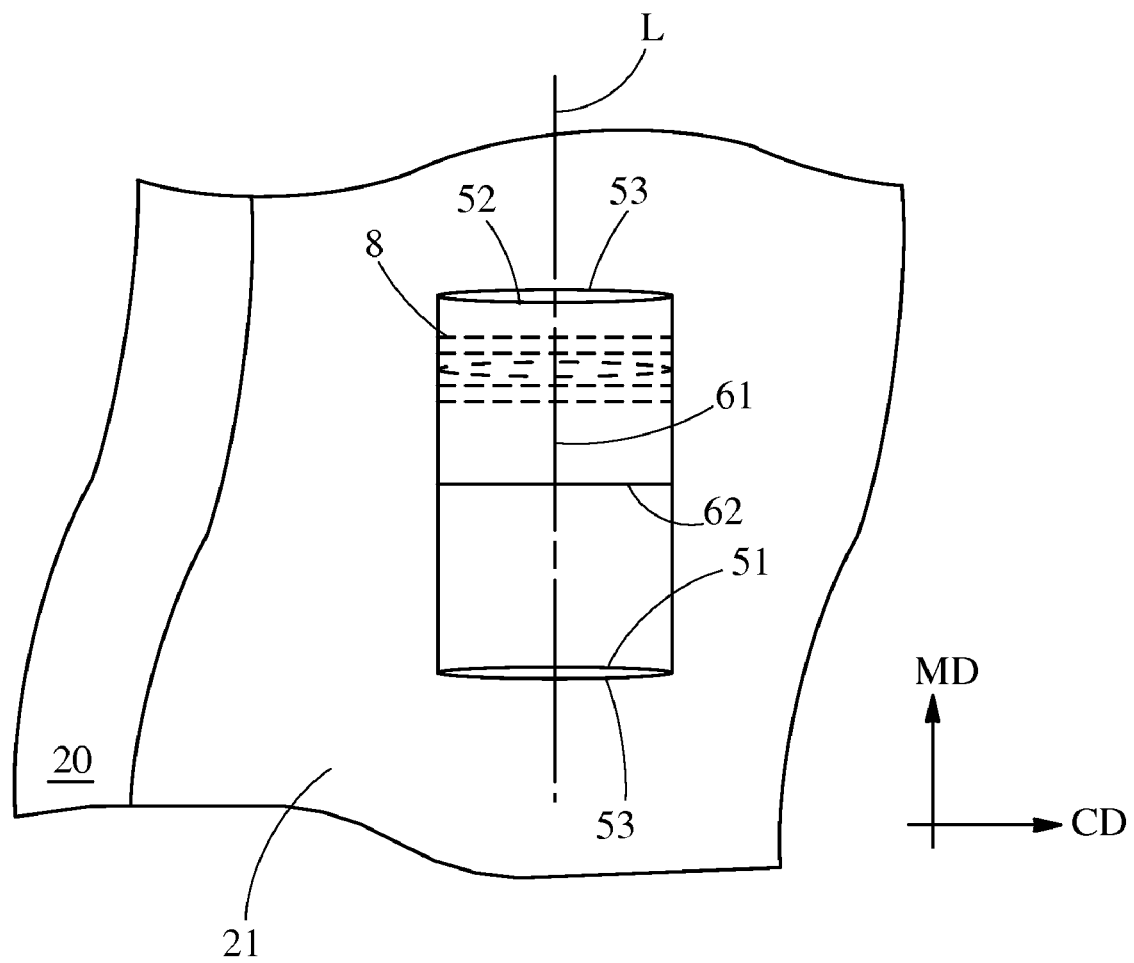
FIG. 5 is a plan view of a portion of the web shown in FIG. 4.

As shown in FIG. 5, cap 7 can have length 61 and a width 62. The length 61 of cap 7 is taken to be between the first opening 51 and second opening 52. Cap 7 can also have a width 62 taken to be the maximum dimension of the cap 7 as measured orthogonal to the length 61 of the cap 7. The plane aspect ratio of the cap 7 can be defined as the ratio between the length 61 and the width 62 of cap 7. The aspect ratio of the cap 7 can be greater than about 0.5. The aspect ratio of the cap 7 can be greater than about 1. The aspect ratio of the cap 7 can be greater than about 1.5. The aspect ratio of the cap 7 can be greater than about 2. In general, it is thought that caps 7 having a higher aspect ratio can be more noticeable to an observer of the laminate web 1 and might also better resist fluid flow along the surface of web 1 in a direction orthogonal to the longitudinal axis L of the tuft 6.

Caps 7 in laminate web 1 are thought to mask or partially mask fluid that is collected by the laminate web 1 and remains in the capillaries between fibers 8 forming tuft 6. Such a laminate web employed in an absorbent article such as a wipe, a sanitary napkin, a tampon, or a diaper can be appealing to the user (or caregiver) in that potentially unsightly urine, menses, feces, or other liquid retained in the capillaries between fibers 8 forming tuft 6 will be obscured or partially obscured from the viewer. In an absorbent article such as a sanitary napkin, in absence of the caps 7, tufts 6 can essentially have the color of menses, which might be unattractive to the user of the sanitary napkin. The caps cover or partially cover tufts in which menses is held and can make the laminate web 1 appear less red or even allow the laminate web 1 to maintain its virgin color (e.g. prior to insult by a fluid).

If the second precursor web 21 and cap 7 extending there from is a polymer film comprising a whitener, such as titanium dioxide, the caps 7 can be more effective at obscuring materials held in the capillaries of the tufts 6 from view. Such caps 7 can better maintain a perceived color of white, which many consumers associate with cleanliness.

The caps 7 can have an opacity greater than about 10%, greater than about 20%, greater than about 30%, greater than about 40%, greater than about 50%, greater than about 60%, greater than about 70%, greater than about 80%, or greater than about 90%. The cap can be opaque. The second precursor web can have an opacity. The opacity of the caps 7 can be less than the opacity of the second precursor web 21 from which the caps 7 extend, for instance as a result of stretching of the precursor web 21 to form cap 7. The caps 7 can have an opacity that is between about 80% and about 95% of the opacity of the second precursor web. The caps 7 can have an opacity that is between about 50% and about 95% of the opacity of the second precursor web. The caps can have an opacity that is between about 35% and about 95% of the opacity of the second precursor web. The greater the opacity of the caps 7, the more effective the caps 7 might be at obscuring liquids that held in the capillaries of the tufts 6. The caps 7 can have an opacity less than about 90% of the opacity of the second precursor web 21. The caps 7 can have an opacity less than about 75% of the opacity of the second precursor web 21. The caps 7 can have an opacity less than about 50% of the opacity of the second precursor web 21.

Second precursor web 21 can have a polymer film thickness t and the cap 7 can have a cap thickness tc. Being that the caps 7 are integral extensions of the second precursor web 21 and formed by stretching the polymer film out of plane of the first surface 13 of the second precursor web 21, the cap thickness tc of a portion of the cap 7 can be less than the polymer film thickness t. That is, the polymer film that is extended to form a cap 7 is thinned at least some portion of the cap 7 relative to the planar portion of the polymer film from which the cap 7 extends. The cap thickness tc may not be uniform about the entire first opening 51 and/or second opening 52. The cap thickness tc at a distal portion of the cap 7 may be the same or less than the polymer film thickness t. The cap thickness tc at a distal portion of the cap 7 may be about the same or less than the polymer film thickness t and the cap thickness tc at a portion of the cap 7 between the distal portion of the cap 7 and the polymer film may be less than the polymer film thickness t. Thinning of the cap 7 may provide for caps 7 having a soft hand. Further, because the cap 7 might be thin and might readily be deformed, the characteristics of the tuft 6 underlying the cap 7 might govern the tactile impression imparted by the tuft 6 having a cap 7. Therefore, the characteristics of the tuft 6 can be important to the tactile impression imparted by the laminate web 1.

Figure 6:
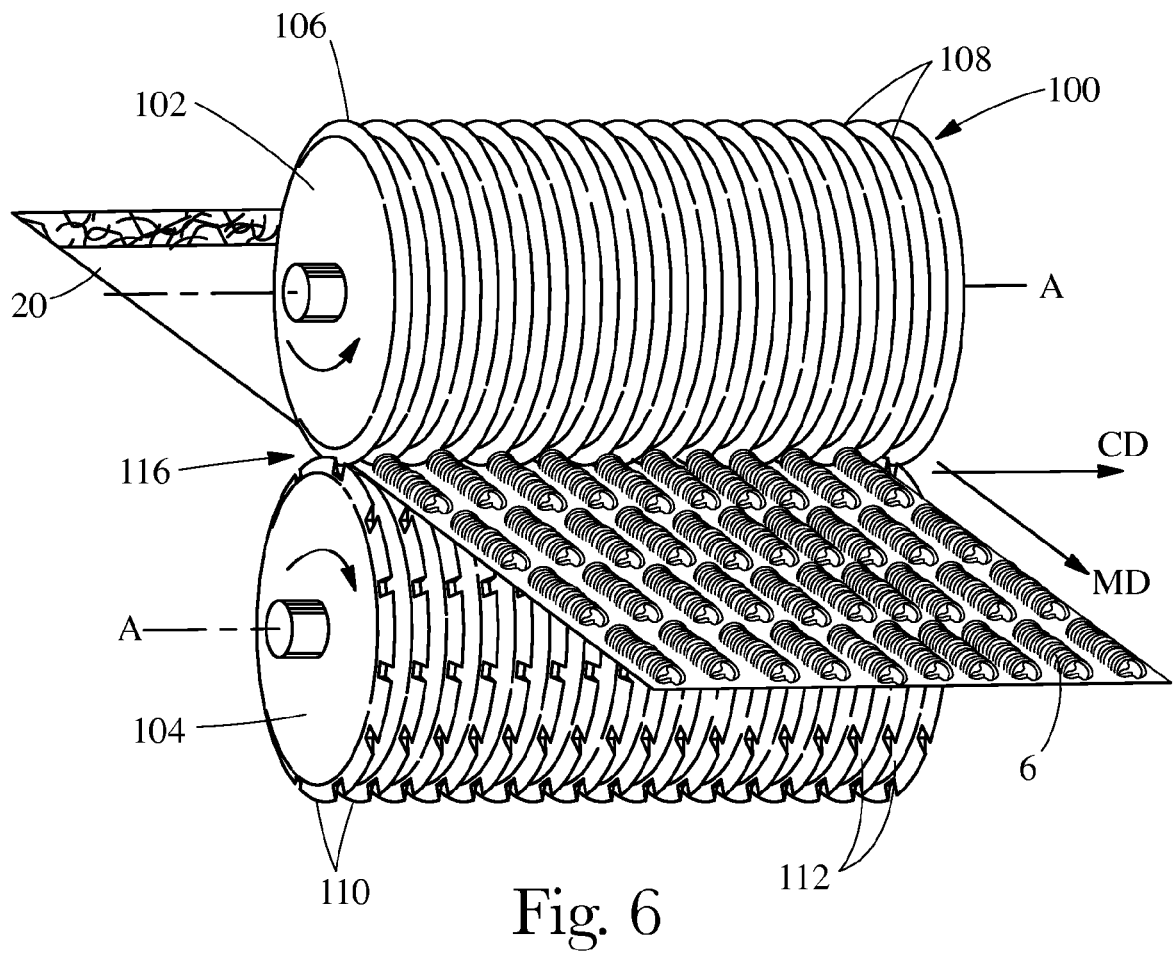
FIG. 6 is a perspective view of an apparatus for forming the web of the present invention.

Referring to FIG. 6 there is shown an apparatus and method for making web 1 of the present invention. The apparatus 100 comprises a pair of intermeshing rolls 102 and 104, each rotating about an axis A, the axes A being parallel in the same plane. Roll 102 comprises a plurality of ridges 106 and corresponding grooves 108 which extend unbroken about the entire circumference of roll 102. Roll 104 is similar to roll 102, but rather than having ridges that extend unbroken about the entire circumference, roll 104 comprises a plurality of rows of circumferentially-extending ridges that have been modified to be rows of circumferentially-spaced teeth 110 that extend in spaced relationship about at least a portion of roll 104. The individual rows of teeth 110 of roll 104 are separated by corresponding grooves 112. In operation, rolls 102 and 104 intermesh such that the ridges 106 of roll 102 extend into the grooves 112 of roll 104 and the teeth 110 of roll 104 extend into the grooves 108 of roll 102. The intermeshing is shown in greater detail in the cross sectional representation of FIG. 7, discussed below. Both or either of rolls 102 and 104 can be heated by means known in the art such as by using hot oil filled rollers or electrically-heated rollers.

In FIG. 6, the apparatus 100 is shown in a configuration having one patterned roll, e.g., roll 104, and one non-patterned grooved roll 102. However, in certain embodiments it may be preferable to use two patterned rolls 104 having either the same or differing patterns, in the same or different corresponding regions of the respective rolls. Such an apparatus can produce webs with tufts 6 protruding from both sides of the web 1.

The method of making a web 1 of the present invention in a continuous process is depicted in FIG. 6. Web 1 can be made by mechanically deforming precursor webs, such as first and second precursor webs, 20 and 21 that can each be described as generally planar and two dimensional prior to processing by the apparatus shown in FIG. 5. By "planar" and "two dimensional" is meant simply that the webs start the process in a generally flat condition relative to the finished web 1 that has distinct, out-of-plane, Z-direction three-dimensionality due to the formation of tufts 6. "Planar" and "two-dimensional" are not meant to imply any particular flatness, smoothness or dimensionality.

The process and apparatus of the present invention is similar in many respects to a process described in U.S. Pat. No. 5,518,801 entitled "Web Materials Exhibiting Elastic-Like Behavior" and referred to in subsequent patent literature as "SELF" webs, which stands for "Structural Elastic-like Film". However, there are significant differences between the apparatus and process of the present invention and the apparatus and process disclosed in the '801 patent, and the differences are apparent in the respective webs produced thereby. As described below, the teeth 110 of roll 104 have a specific geometry associated with the leading and trailing edges that permit the teeth to essentially "punch" through the precursor webs 20, 21 as opposed to, in essence, deforming the web. In a two layer laminate web 1 the teeth 110 urge fibers from a first precursor web 20 simultaneously out-of-plane and through second precursor web 21, which is ruptured, so to speak, by the teeth 110 pushing the fibers 8 through the plane of second precursor web 21 to form tufts 6 and caps 7 Therefore, a web 1 of the present invention can have tufts 6 of non-looped fibers 18 and/or "tunnel-like" tufts 6 of looped, aligned fibers 8 extending through and away from the surface 13 of a first side 3, unlike the "tent-like" rib-like elements of SELF webs which each have continuous side walls associated therewith, i.e., a continuous "transition zone," and which do not exhibit rupturing of second precursor web 21.

Precursor webs 20 and 21 are provided either directly from their respective web making processes or indirectly from supply rolls and moved in the machine direction to the nip 116 of counter-rotating intermeshing rolls 102 and 104. The precursor webs are preferably held in a sufficient web tension so as to enter the nip 116 in a generally flattened condition by means well known in the art of web handling. As each precursor web 20, 21 goes through the nip 116 the teeth 110 of roll 104 which are intermeshed with grooves 108 of roll 102 simultaneously urge portions of first precursor web 20 out of the plane of first precursor web 20 and through the plane of second precursor web 21 to form tufts 6. In effect, teeth 110 "push" or "punch" fibers of first precursor web 20 through the plane of second precursor web 21.

As the tip of teeth 110 push through first and second precursor webs 20, 21 the portions of the fibers of first precursor web 20 that are oriented predominantly in the CD across teeth 110 are urged by the teeth 110 out of the plane of first precursor web 20. Fibers can be urged out of plane due to fiber mobility, or they can be urged out of plane by being stretched and/or plastically deformed in the Z-direction. Portions of first precursor web 20 urged out of plane by teeth 110 push through the plane of the first surface 13 of second precursor web 21, which due to its relatively lower extensibility, ruptures, thereby resulting in formation of caps 7 and tufts 6 on first side 3 of web 1. Fibers of first precursor web 20 that are predominantly oriented generally parallel to the longitudinal axis L, i.e., in the MD of precursor web 20 as shown in FIG. 1, are simply spread apart by teeth 110 and remain substantially in their original, randomly-oriented condition. This is why the looped fibers 8 can exhibit the unique fiber orientation in embodiments such as the one shown in FIGS. 1-4, which is a high percentage of fibers of each tuft 6 having a significant or major vector component parallel to the transverse axis T of tuft 6.

It can be appreciated by the forgoing description that when web 1 is made by the apparatus and method of the present invention that the precursor webs 20, 21 should possess differing material properties with respect to the ability of the precursor webs to elongate before failure, e.g., failure due to tensile stresses. In particular, a nonwoven first precursor web 20 can have greater fiber mobility and/or greater fiber elongation characteristics relative to second precursor web 21, such that the fibers thereof can move or stretch sufficiently to form tufts 6 while the second precursor web 21 ruptures, i.e., does not stretch to the extent necessary to form tufts.

The degree to which the fibers of nonwoven precursor webs are able to extend out of plane without plastic deformation can depend upon the degree of inter-fiber bonding of the precursor web. For example, if the fibers of a nonwoven precursor web are only very loosely entangled to each other, they will be more able to slip by each other and therefore be more easily extended out of plane to form tufts. On the other hand, fibers of a nonwoven precursor web that are more strongly bonded, for example by high levels of thermal point bonding, hydroentanglement, or the like, will more likely require greater degrees of plastic deformation in extended out-of-plane tufts. Therefore, in one embodiment, first precursor web 20 can be a nonwoven web having relatively low inter-fiber bonding.

For a given maximum strain (e.g., the strain imposed by teeth 110 of apparatus 100), second precursor web 21 must actually fail under the tensile loading produced by the imposed strain to locally (i.e., in the area of strain) fail in tension, thereby producing openings 4 through which tufts 6 can extend. If second precursor web 21 merely deforms or stretches in the region of induced strain, but does not actually fail, thereby producing an opening 4 therein, a tuft 6 may not result. In one embodiment second precursor web 21 has an elongation to break in the range of 1%-5%. While the actual required elongation to break depends on the strain to be induced to form web 1, it is recognized that for most embodiments, second precursor web 21 can exhibit a web elongation-to-break of 6%, 7%, 8%, 9%, 10%, or more. It is also recognized that actual elongation-to-break can depend on the strain rate, which, for the apparatus shown in FIG. 6 is a function of line speed. Elongation to break of webs used in the present invention can be measured by means known in the art, such as by standard tensile testing methods using standard tensile testing apparatuses, such as those manufactured by Instron, MTS, Thwing-Albert, and the like.

Furthermore, relative to first precursor web 20, second precursor web 21 can have lower elongation-to-break (i.e., elongation-to-break of the film) such that, rather than extending out-of-plane to the extent of the tufts 6, second precursor web 21 ruptures in tension under the strain produced by the formation of tufts 6, e.g., by the teeth 110 of apparatus 100. In general, second precursor web 21 can have an elongation to break of at least 10% less than the first precursor web 20, at least 30% less, more preferably at least 50% less, and even more preferably at least about 100% less than that of first precursor web 20. Relative elongation to break values of webs used in the present invention can be measured by means known in the art, such as by standard tensile testing methods using standard tensile testing apparatuses, such as those manufactured by Instron, MTS, Thwing-Albert, and the like.

The number, spacing, and size of tufts 6 can be varied by changing the number, spacing, and size of teeth 110 and making corresponding dimensional changes as necessary to roll 104 and/or roll 102. This variation, together with the variation possible in precursor webs 20, 21 permits many varied webs 1 to be made for many purposes. For example, a web 1 made from a first precursor web 20 comprising a relatively low basis weight nonwoven web of plastically-extensible spunbond polymer fibers and a second precursor web 21 comprising relatively low-extensible synthetic polymer film could be could be used as a terry cloth-like fabric for semi-durable or durable clothing, or for personal care items as are described in WO 01/76523. As described more fully below, a web 1 comprising a nonwoven/film first precursor web/second precursor web combination can also be used as a component in disposable absorbent articles.

Figure 7:
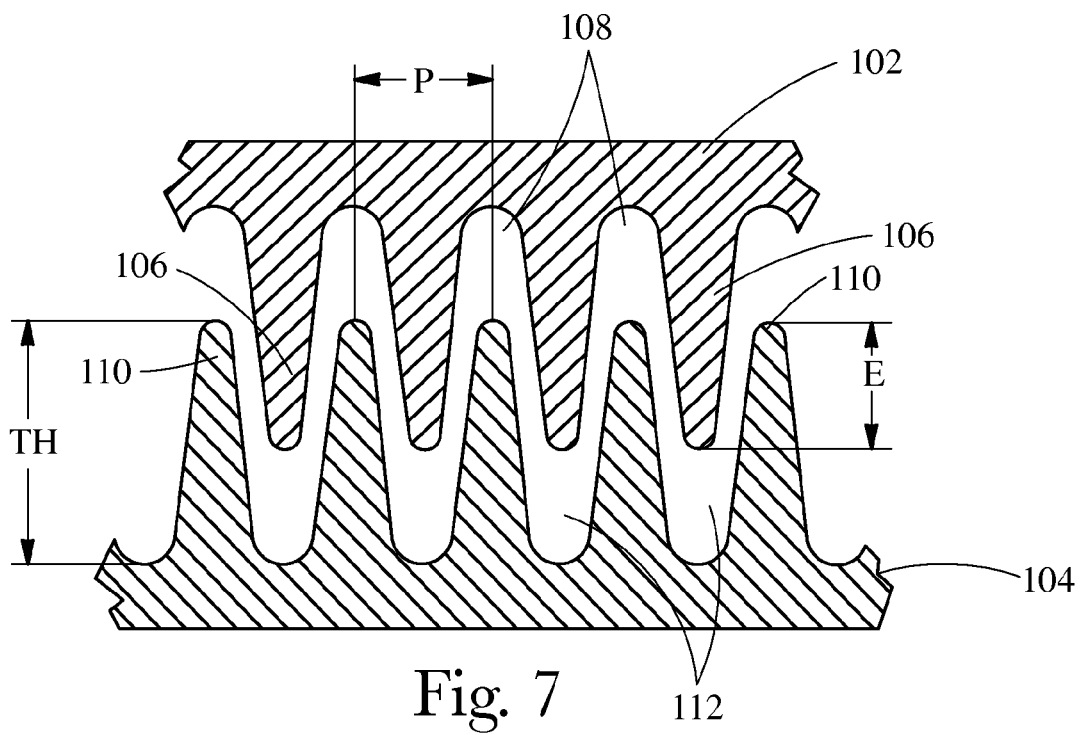
FIG. 7 is a cross-sectional depiction of a portion of the apparatus shown in FIG. 6.

FIG. 7 shows in cross section a portion of the intermeshing rolls 102 and 104 and ridges 106 and teeth 110. As shown teeth 110 have a tooth height TH (note that TH can also be applied to ridge height; in one embodiment tooth height and ridge height are equal), and a tooth-to-tooth spacing (or ridge-to-ridge spacing) referred to as the pitch P. As shown, depth of engagement E is a measure of the level of intermeshing of rolls 102 and 104 and is measured from tip of ridge 106 to tip of tooth 110. The depth of engagement E, tooth height TH, and pitch P can be varied as desired depending on the properties of precursor webs 20, 21 and the desired characteristics of web 1. For example, in general, the greater the level of engagement E, the greater the necessary elongation or fiber-to-fiber mobility characteristics the fibers of first precursor web 20 must possess. Also, the greater the density of tufts 6 desired (tufts 6 per unit area of web 1), the smaller the pitch should be, and the smaller the tooth length TL and tooth distance TD should be, as described below.

Figure 8:
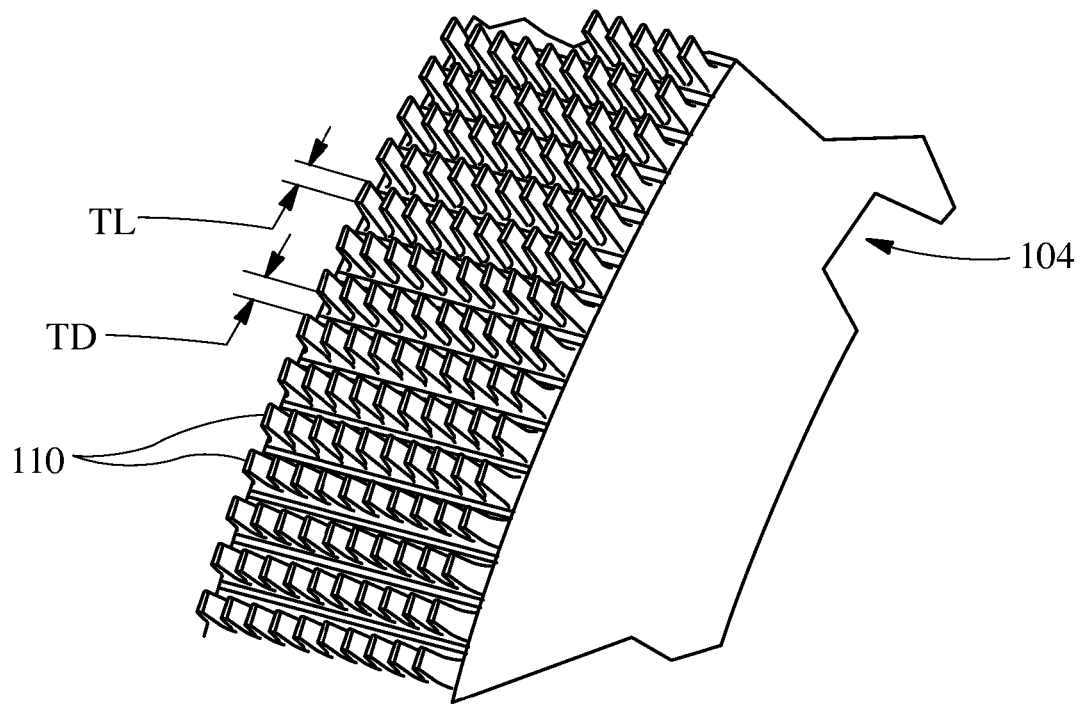
FIG. 8 is a perspective view of a portion of the apparatus for forming one embodiment the web of the present invention.

FIG. 8 shows one embodiment of a roll 104 having a plurality of teeth 110 useful for making a terry cloth-like web 1 from a nonwoven first precursor web 20 having a basis weight of between about 60 gsm and 100 gsm, or about 80 gsm and a polyolefin film (e.g., polyethylene or polypropylene) second precursor web 21 having a density of about 0.91-0.94 and a basis weight of about 20 gsm.

Figure 9:
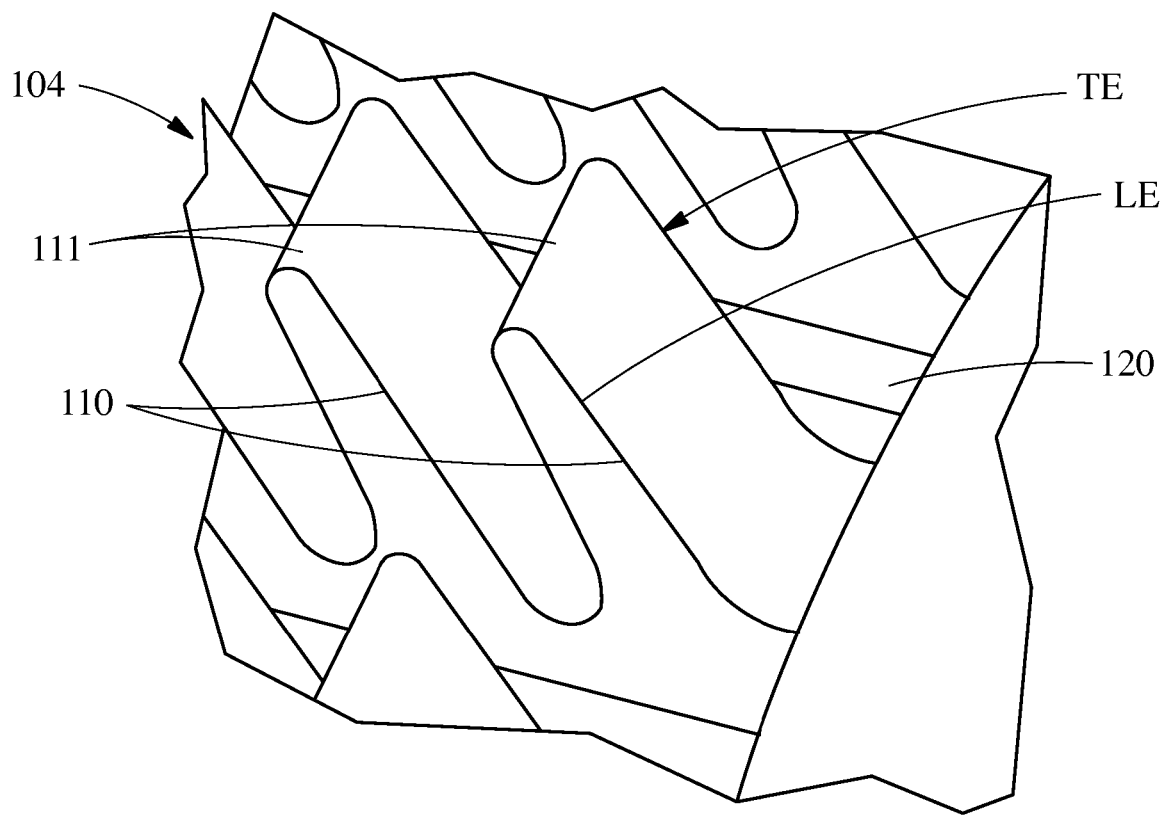
FIG. 9 is an enlarged perspective view of a portion of the apparatus for forming the web of the present invention.

An enlarged view of teeth 110 is shown in FIG. 9. In this embodiment of roll 104 teeth 110 have a uniform circumferential length dimension TL measured generally from the leading edge LE to the trailing edge TE at the tooth tip 111 of about 1.25 mm and are uniformly spaced from one another circumferentially by a distance TD of about 1.5 mm. For making a terry-cloth web 1 from web 1 having a total basis weight in the range of about 60 to about 100 gsm, teeth 110 of roll 104 can have a length TL ranging from about 0.5 mm to about 3 mm and a spacing TD from about 0.5 mm to about 3 mm, a tooth height TH ranging from about 0.5 mm to about 5 mm, and a pitch P between about 1 mm (0.040 inches) and about 5 mm (0.200 inches). Depth of engagement E can be from about 0.5 mm to about 5 mm (up to a maximum equal to tooth height TH). Of course, E, P, TH, TD and TL can be varied independently of each other to achieve a desired size, spacing, and area density of tufts 6 (number of tufts 6 per unit area of web 1).

As shown in FIG. 9, each tooth 110 has a tip 111, a leading edge LE and a trailing edge TE. The tooth tip 111 is elongated and has a generally longitudinal orientation, corresponding to the longitudinal axes L of tufts 6 and discontinuities 16. It is believed that to get the tufted, looped tufts 6 of the web 1 that can be described as being terry cloth-like, the LE and TE should be very nearly orthogonal to the local peripheral surface 120 of roll 104. As well, the transition from the tip 111 and LE or TE should be a sharp angle, such as a right angle, having a sufficiently small radius of curvature such that teeth 110 push through second precursor web 21 at the LE and TE. Without being bound by theory, it is believed that having relatively sharply angled tip transitions between the tip of tooth 110 and the LE and TE permits the teeth 110 to punch through precursor web 20 and rupture precursor web 21 "cleanly", that is, locally and distinctly. Further, a sharp transition may provide for formation of the first opening 51 and second opening 52. For polymer film having microtexture such as micro apertures, microbubbles, or other such relatively small structures in the polymer film (relative to the spacing between tufts 6), stress concentrations in the polymer film arising as a result of the microtexture might provide for formation of caps 7, as opposed to having the tuft erupt through the polymer film without formation of a caps 7. When so processed, the web 1 is not imparted with any particular elasticity, beyond what the precursor webs 20 and 21 may have possessed originally.

Therefore, from the above description, it is understood that in one embodiment web 1 can be described as being a laminate web formed by selective mechanical deformation of at least a first and second precursor webs, the first precursor web being a nonwoven web and the second precursor web being a polymer film, the laminate web having a first side, the first side comprising the second precursor web and a plurality of discrete tufts comprising fibers integral with and extending from the nonwoven web, each of the tufts having a tuft base proximal to the nonwoven web and a distal portion opposing the tuft base, at least part of the distal portion of each of the tufts is covered by cap, each cap being an integral extension of the polymer film extending over the distal portion of a discrete tuft, the cap comprising a first opening comprising a location of rupture in the polymer film above which the tuft extends.

While not wishing to be bound by theory, it is believed that if the fibers of the first precursor web have a highly curvilinear shape, e.g., curled fibers, the resultant tufts 6 will have more looped fibers 8 and less non-looped fibers 18 as compared to more linear fiber conformations. It is believed that such fiber conformations have a lesser chance of bridging between two adjacent teeth, and, as a result they are less prone to be stretched beyond their breaking point, and thus have a greater chance of forming complete loop structures. Furthermore, such curvilinear-shaped fibers can be made by using eccentric bicomponent fibers, or side-by-side bicomponent fibers, such as bicomponent fibers consisting of polyethylene and nylon.

It has been found that certain nonwoven webs, such as carded webs comprising staple-length fibers, when used as first precursor web 20 produce very few looped fibers 8 in tufts 6, so that the tufts 6 produced in these webs cannot be described as comprising a plurality of looped, aligned fibers 8 as described above with respect to FIGS. 1-4. Instead, carded nonwoven webs can produce tufts 6 having few, if any, looped, aligned fibers 8, and many, if not all, non-aligned fibers and/or non-looped fibers 18. It is believed that the non-alignment of fibers in tufts 6 made from carded webs is due in part to the nature of the fiber content of carded webs. Staple fibers are not "endless," but instead have a predetermined length on the order of about 15 mm to about 100 mm, and, more typically from about 40 mm to about 80 mm. Therefore, when a carded web is processed by the apparatus described with respect to FIG. 6, it is believed that there is a much greater likelihood that a loose fiber end will be in the vicinity of a tuft 6 and thus produce a non-looped fiber end in tuft 6. Furthermore, often staple fibers do not have the same elongation characteristics of spunbond or meltblown fibers, for example. However, even if tufts 6 have no looped fibers, the fibrous tufts can nevertheless provide a softness benefit and produce a web having terry cloth-like characteristics.

If a woven first precursor web 20 is utilized, the formation and structure of tufts 6 can be very close to the same as that exhibited by tufts 6 formed from nonwoven webs. For example, if a woven first precursor web 20 has extensible warp and/or weft threads predominantly oriented in a cross machine direction, upon being processed by the apparatus 100 described above, the teeth 110 tend to separate the machine direction threads (either warp or weft) and only urge out of plane the cross-machine direction threads. Thus, the web 1 produced from a woven first precursor web 20 can look and feel very much like terry cloth fabric.

In some embodiments, first precursor web 20 is a nonwoven web in which there are minimal fiber-to-fiber bonds. For example, the precursor web can be a nonwoven web having a pattern of discrete thermal point bonds, as is commonly known in the art for nonwoven webs. In general, however, it is desirable to minimize the number of bond points and maximize the spacing so as to allow for maximum fiber mobility and dislocation during formation of tufts 6. In general, using fibers having relatively high diameters, and/or relatively high extension to break, and/or relatively high fiber mobility, might result in better and more distinctly formed tufts 6.

Although web 1 is disclosed as a two layer web made from two precursor webs, it is not necessary that it be limited to two layers. For example, a three-layer or more laminate can be made from three precursor webs. For example, web 1 could comprise the top sheet, secondary topsheet, and core of hygiene products. In general, it is not necessary that adhesive or other bonding means be utilized to make laminate web 1.

The constituent layers of web 1 (e.g., precursor webs 20 and 21 and any other layers) can be held in a face-to-face laminated relationship by virtue of the "locking" effect of the tufts 6 that extend through openings 4 in second precursor web 21. In some embodiments it may be desirable to use adhesives or thermal bonding or other bonding means, depending on the end use application of web 1. For example, a web 1 comprising bicomponent fiber nonwoven webs can be through-air bonded after formation of tufts 6 to provide for layer-to-layer adhesion for greater peel strength. Additionally, it may be desirable to apply adhesive to at least a portion of one of the precursor webs. For example, in some embodiments adhesive, chemical bonding, resin or powder bonding, or thermal bonding between layers can be selectively applied to certain regions or all of the precursor webs. In the case of adhesive application, for example, adhesive can be applied in a continuous manner, such as by slot coating, or in a discontinuous manner, such as by spraying, extruding, and the like. Discontinuous application of adhesive can be in the form of stripes, bands, droplets, and the like.

In a multilayer web 1 each precursor web can have different material properties, thereby providing web 1 with beneficial properties. For example, web 1 comprising two (or more) precursor webs, e.g., first and second precursor webs, can have beneficial fluid handling properties for use as a topsheet on a disposable absorbent article, as described below. For superior fluid handling, for example, first precursor web 20 can be comprised of relatively hydrophilic fibers. Second precursor web 21 can be polymer film, e.g., a polyethylene film, and can be hydrophobic or rendered hydrophobic. Fluid deposited upon the upper relatively hydrophobic polymer film might be quickly acquired by hydrophilic tufts 6.

One driving mechanism for rapid fluid transport might be the capillary structures formed by the generally aligned fibers 8, 18 of tufts 6. The fibers 8, 18 form directionally-aligned capillaries between adjacent fibers, and the capillary action is enhanced by the general convergence of fibers near the base 17 of tufts 6.

It is believed that the rapid fluid transport might further be increased due to the ability of fluid to enter the web 1 via the voids 10 defined by looped tufts 6. This "lateral entry" capability and/or capillary action, and/or the hydrophilicity gradient afforded by the structure of web 1 might make web 1 an ideal material for optimal fluid handling for disposable absorbent articles.

Depending on the precursor webs 20 and 21 utilized and the dimensional parameters of rolls 102 and, including teeth 110, web 1 can exhibit a wide range of physical properties. The web 1 can exhibit a range of texture subjectively experienced as ranging from softness to roughness, an absorbency ranging from non-absorbent to very absorbent, a bulkiness ranging from relatively low bulk to relatively high bulk; a tear strength ranging from low tear strength to high tear strength; an elasticity ranging from non-elastic to at least 100% elastically extensible, a chemical resistance ranging from relatively low resistance to high resistance, depending on the chemical considered, and many other variable parameters generally described as shielding performance, alkali resistance, opacity, wiping performance, water absorptivity, oil absorptivity, moisture permeability, heat insulating properties, weatherability, high strength, high tear force, abrasion resistance, electrostatic controllability, drape, dye-affinity, safety and the like. In general, depending on the elongation properties of the first precursor web 20, the dimensions of apparatus 100 can be varied to produce a web 1 having a wide range of dimensions associated with tufts 6, including the height h (as shown in FIG. 3), and spacing (including area density of tufts 6). Additionally, the tufts may be easily patterned into lines, filled forms, and selective regions of the laminate web by having the desired pattern displayed in the teeth 110 on the roll 104.

The laminate web 1 can comprise a lotion composition. A lotion composition on the body facing surface of an absorbent article has been found to be able to modulate skin properties and conditions for the wearer. The lotion composition can be a semisolid lotion that melts when the absorbent article is worn against a body. The lotion can be a hydrophobic semisolid lotion which can contribute to reducing rewet from the absorbent article to the wearer's body, thereby improving the wearing experience. The tufts 6 can be substantially free of lotion, thereby preserving the fluid acquisition properties of the tufts 6. Lotion composition can be applied to the laminate web 1 using a kiss roll. Lotion composition can be applied to the caps 7. The lotion composition can comprise petrolatum. The lotion composition can include lotion compositions disclosed in U.S. Pat. No. 5,968,025; U.S. Pat. No. 6,627,787; U.S. Pat. No. 6,498,284; U.S. Pat. No. 6,426,444; U.S. Pat. No. 6,586,652; U.S. Pat. No. 3,489,148; U.S. Pat. Nos. 6,503,526; 6,287,581; U.S. Pat. No. 6,475,197; U.S. Pat. No. 6,506,394; U.S. Pat. No. 6,503,524; U.S. Pat. No. 6,626,961; U.S. Pat. No. 6,149,934; U.S. Pat. No. 6,515,029; U.S. Pat. No. 6,534,074; U.S. Pat. No. 6,149,932WO 2000038747; or EP-A 927,050, or combinations thereof. The lotion composition can be applied such that more than about seventy five percent of said lotion composition by mass per square centimeter is applied to said polymer film, That is, for a particular square centimeter of laminate comprising a lotion composition, more than about seventy five percent by mass is applied to the polymer film. The lotion composition can be applied such that more than about ninety percent of said lotion composition by mass per square centimeter is applied to the polymer film, Web 1 may be used for a wide variety of applications, including various filter sheets such as air filter, bag filter, liquid filter, vacuum filter, water drain filter, and bacterial shielding filter; sheets for various electric appliances such as capacitor separator paper, and floppy disk packaging material; various industrial sheets such as tacky adhesive tape base cloth, oil absorbing material, and paper felt; various wiper sheets such as wipers for homes, services and medical treatment, printing roll wiper, wiper for cleaning copying machine, baby wipers, and wiper for optical systems; various medicinal and sanitary sheets, such as surgical gown, gown, covering cloth, cap, mask, sheet, towel, gauze, base cloth for cataplasm, diaper, diaper liner, diaper cover, feminine napkin covers, feminine napkin or diaper acquisition layer (underneath the cover layer), diaper core, tampon liners, tampon overwraps, base cloth for adhesive plaster, wet towel, and tissue; various sheets for clothes, such as padding cloth, pad, jumper liner, and disposable underwear; various life material sheets such as base cloth for artificial leather and synthetic leather, table top, wall paper, blind, wrapping, and packages for drying agents, shopping bag, suit cover, and pillow cover; various agricultural sheets, such as ground covers and erosion control devices, cooling and sun light-shielding cloth, lining curtain, sheet for overall covering, light-shielding sheet, wrapping materials of pesticides, underlining paper of pots for seeding growth; various protection sheets such as fume prevention mask and dust prevention mask, laboratory gown, and dust preventive clothes; various sheets for civil engineering building, such as house wrap, drain material, filtering medium, separation material, overlay, roofing, tuft and carpet base cloth, wall interior material, soundproof or vibration reducing sheet, and curing sheet; and various automobile interior sheets, such as floor mat and trunk mat, molded ceiling material, head rest, and lining cloth, in addition to a separator sheet in alkaline batteries. Other uses include utilizing web 1 as a wipe for personal cleansing or hygiene, such as for a baby wipe, facial cloth or wipe, or body cloth.

In one embodiment, web 1 or a composite comprising web 1 can be utilized as a fecal material storage element. Web 1 can be utilized as a secondary topsheet or sublayer when it is disposed under an apertured web or film to accept and hold low viscosity feces or viscous bodily waste away from a wearer's skin after defecation. Embodiments of the present invention having larger total three dimensional volume within the web or between the tufts 6 generally provide a greater capacity for storage of low viscosity feces. Absorbent articles employing such fecal material storage elements, or sublayers, are described in U.S. Pat. Nos. 5,941,864; 5,957,906; 6,018, 093; 6,010,491; 6,186,992; and 6,414,215, among others.

In one embodiment, web 1 comprises a nonwoven first precursor web 20 comprising a spunbond nonwoven having a basis weight of about 80 gsm, and comprising polyethylene/polypropylene (sheath/core) bicomponent fibers having an average diameter of about 33 microns, and a second precursor web comprising a polyethylene film having a basis weight of 20 gsm. In this embodiment, web 1 has about 24 tufts 6 per square centimeter, the tufts 6 having a plurality of looped, aligned fibers 8, each of which has an average fiber diameter of about 18 microns. A web of this type can be beneficially used as a topsheet for disposable absorbent articles, as shown below with reference to FIG. 10. For example, such a web 1 is fluid impermeable except in the regions of the tufts 6 which can wick fluid from the first side 3 of web 1 to the second side 5.

Figure 10:
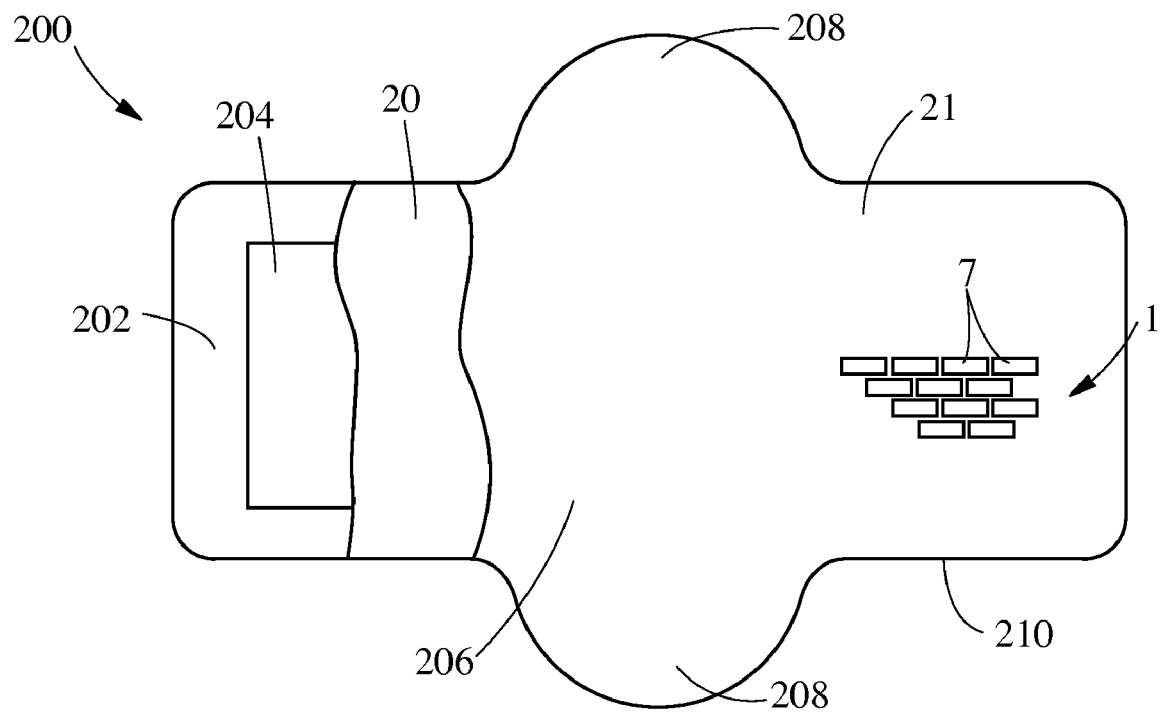
FIG. 10 is a partial cutaway plan view of a sanitary napkin of the present invention.

FIG. 10 shows in partial cut away plan view a sanitary napkin having as one of its components a web 1 of the present invention. In general, sanitary napkin 200 comprises a backsheet 202, a topsheet 206 and an absorbent core 204 disposed between the topsheet 206 and backsheet 202 which can be joined about a the periphery 210. The topsheet 206 can comprise web 1. The topsheet 206 can be in a facing relationship with the absorbent core 204 and the first precursor web 20 from which the tufts 6 extend can be between the second precursor web 21 and the absorbent core 204. Sanitary napkin 1 can have side extensions, commonly referred to as "wings" 208 designed to wrap the sides of the crotch region of the panties of the user of sanitary napkin 1. Sanitary napkins, including topsheets for use as the body facing surface thereof, are well known in the art and need no detailed description of various alternative and optional designs. In addition to sanitary napkins, web 1 can also be used in a diaper or adult incontinence product or other disposable hygiene products. However, it is noted that web 1 can be used as, or as a component of, one or more of a backsheet, core material, topsheet, secondary topsheet, or wing material. Web 1 can also have multiple layers and comprise a topsheet, secondary topsheet, core, backsheet, or any number of layers.

Web 1 might be especially useful as a topsheet 206 of sanitary napkin 200. Web 1 might be beneficial as a topsheet 206 for sanitary napkins due to the combination of excellent fluid acquisition and distribution to the absorbent core 204, excellent prevention of rewet to the body-facing surface of topsheet 206 when in use, and the ability of the caps 7 to obscure fluid that is retained in the capillaries of tufts 6. Rewet can be a result of at least two causes: (1) squeezing out of the absorbed fluid due to pressure on the sanitary napkin 200; and/or (2) wetness entrapped within or on the topsheet 206. In a desired topsheet 206 both properties, fluid acquisition and fluid retention, are maximized and rewet is minimized. Said differently, a desirable topsheet might exhibit high rates of fluid acquisition, and low levels of rewet.

A topsheet 206 can be made by using a nonwoven first precursor web 20 and a fluid impermeable polyethylene film second precursor web 21. The basis weights of the component webs can be varied, however, in general due to cost and benefit considerations a total basis weight of between about 20 gsm and 80 gsm is desirable for web 1. When made as a film/nonwoven laminate, web 1 can combine the softness and fluid capillarity of fiber tufts and the rewet prevention of a fluid impermeable polymer film. When a sanitary napkin is used having a topsheet 206 comprising web 1 with first side 3 being the body-facing side, and the second side 5 being in fluid communication with an underlying absorbent core, fluid can be acquired by tufts 6 on first side 3 of web 1 and wicked through second precursor web 21 to second side 5 of web 1 which can then be desorbed to the absorbent core 204. Because tufts 6 are discrete and spaced apart, and are separated by a fluid impermeable second precursor web 21, rewet can be minimized. Alternatively, web 1 could be used with first side 3 being the fluid communication side and second side 5 being the body-facing side. This enables the discontinuities 16 to potentially allow fluid to be transported into or through the tufts 6.

Figure 11:
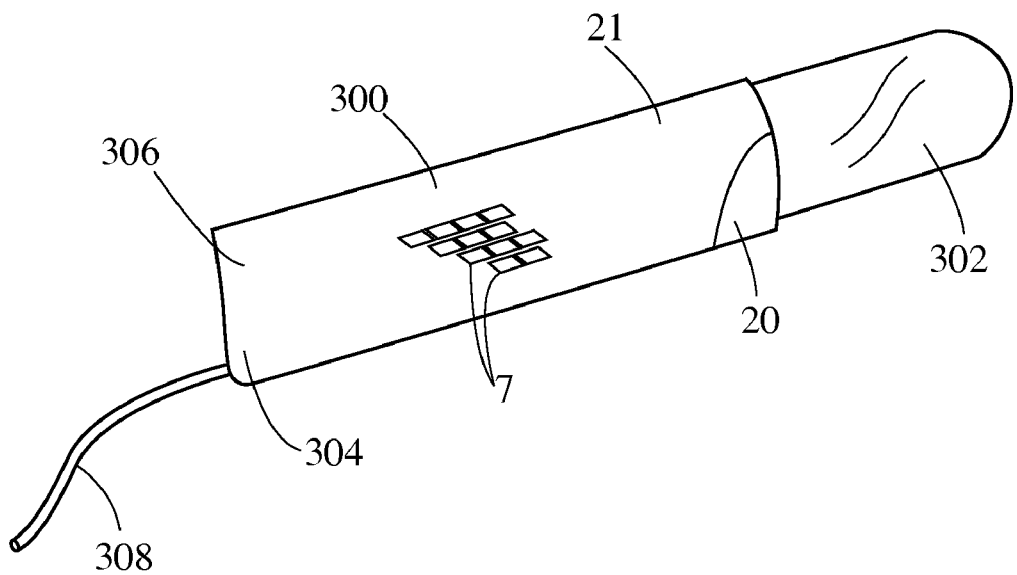
FIG. 11 is a partial cut away perspective view of a tampon of the present invention.

FIG. 11 shows in partial cut away perspective view a catamenial tampon 300 having as one of its components a web 1 of the present invention. In general, tampon 300 comprises a compressed absorbent core 302 and a fluid permeable cover wrap 304 that covers absorbent core 302. Cover wrap 304 may extend beyond one end of absorbent core 302 to form a skirt portion 306. A removal means, such as string 308 can be provided to facilitate removal of the tampon after use. Tampons, including cover wraps for use as the body contacting surface thereof, are well known in the art and need no detailed description of various alternative and optional designs. However, it is noted that web 1 can be used as, or as a component of, one or more of a cover wrap, absorbent core material, or removal means material.

Figure 12:
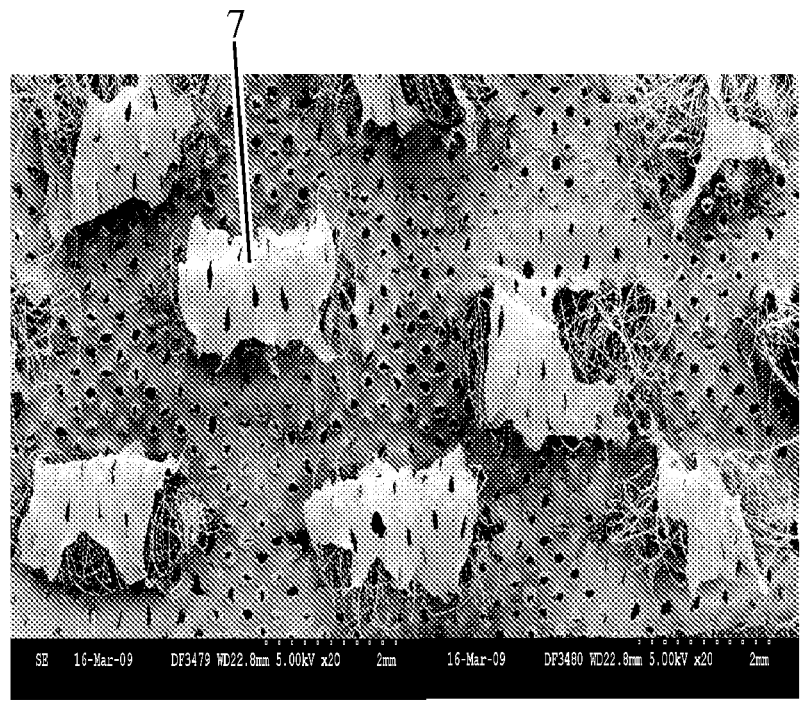
FIGS. 12-14 are scanning electron micrographs of a web of the present invention.

FIG. 12 is a top view scanning electron micrograph (SEM) of a laminate web as disclosed herein. As shown in FIG. 12, a cap 7 covers the distal portion 31 of at least part of a particular tuft 6. In FIG. 12, the cap integrally extends from at least two extension locations 54 on opposite sides of the tuft 6. The extension locations 54 are separated by the first opening 51 and the second opening 52. When viewed from above, the cap 7 covering the distal portion 31 of a particular tuft can help obscure from view fluid, such as menses, held within the capillaries of the fibers 8 forming tuft 6. Also shown in FIG. 12 is microtexture in the polymer web, the microtexture being microapertures 72.

Figure 13:

FIG. 13 is a profile view SEM of a laminate web as disclosed herein. As shown in FIG. 13, cap base 71 proximal the first side 3 of laminate web 1 is narrower than a portion of the cap 7 away from the cap base 71. The cap 7 in FIG. 13 is generally omega ( ) shaped.

Figure 14:
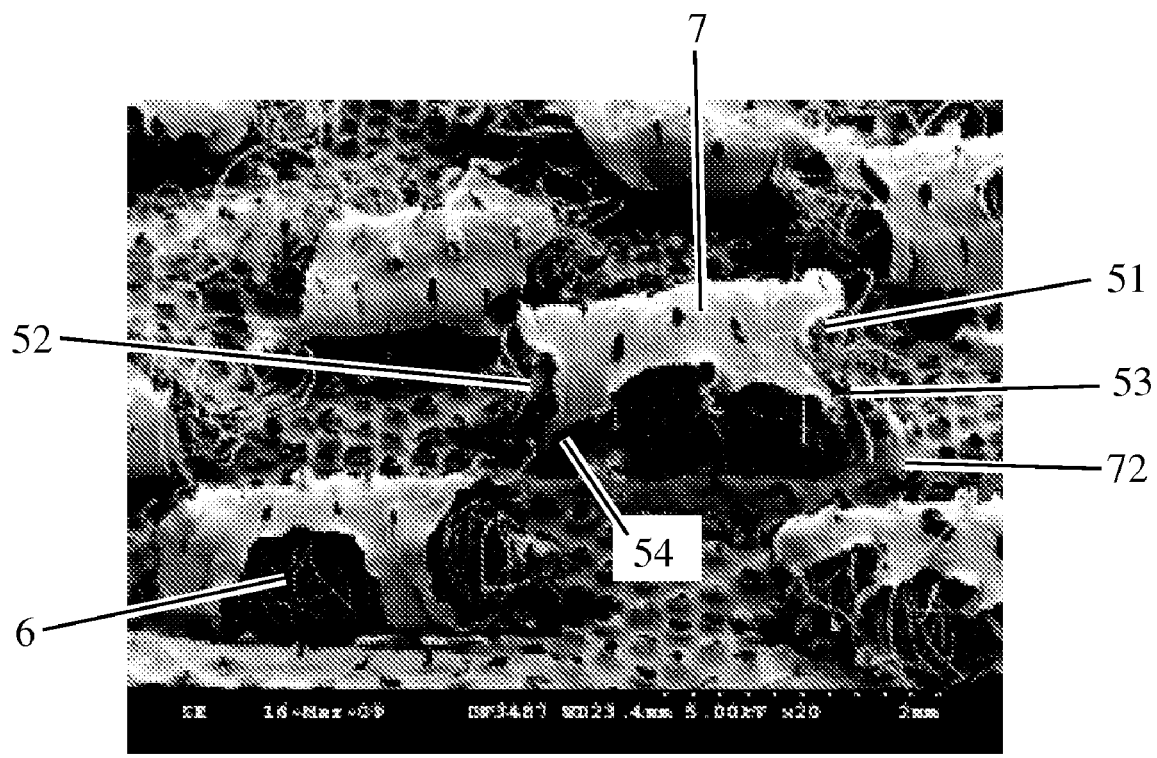

FIG. 14 is an elevated profile view SEM of a laminate web as disclosed herein. As shown in FIG. 14, the cap 7 can have more than two openings such that the cap extends from the first precursor web 21 (polymer film) at more than two discrete locations.

A laminate web 1 that could be used as a topsheet 206 or cover wrap 304 can be fabricated using the apparatus disclosed herein. A suitable material for first precursor web 20 can be a BBA Bico, 28 gsm, GCAS 95001796, 50/50 PE/PP, philic nonwoven, available from BBA Nonwovens. A suitable material for the second precursor web 21 could be Tredegar X-33350 (philic) which is a 100 mesh precursor web, obtainable from Tredegar Corp. Two sets of process parameters listed in Table 1 could be employed to form the laminate web disclosed herein. The teeth 110 could have a uniform circumferential length dimension TL of 0.120 inches spaced from one another circumferentially by a distance TD of 0.060 in., a pitch P of 0.060 in., a depth of engagement E of 0.114 in., a tooth height TL of 0.185 in, a radius of curvature at the tips of teeth 110 and grooves 108 of 0.005 in, and the radius of curvature in the valleys between teeth 110 and grooves 108 of 0.015 in. The temperature of the nonwoven in could be about 25° C. The temperature of the polymer film in could be higher than 25° C. Having the temperature of the polymer film above 25° C., for instance about 50° C., may provide for formation of caps 7. In general, it is thought that modulus of the materials processed, temperature, microtexture of the polymer film, and the web tensions on the upstream side and downstream side of the apparatus might be factors that affect the resulting structure of the laminate.

TABLE 1

| | Elastic Modulus (N/m) | Relaxed Width (mm) | Speed (m/min) | Strain | Tension (N) |
|---|---|---|---|---|---|
| Process 1 | | | | | |
| Nonwoven In | 4043 | 165 | 367.0 | 1.021 | 13.98 |
| Polymer Film In | 1478 | 176 | 367.0 | 1.021 | 1.42 |
| Laminate Out | | 176 | 364.3 | 1.014 | 9.93 |

TABLE 1-continued

| | Elastic Modulus (N/m) | Relaxed Width (mm) | Speed (m/min) | Strain | Tension (N) |
|---|---|---|---|---|---|
| Process 2 | | | | | |
| Nonwoven In | 1896 | 165 | 367.0 | 1.029 | 9.16 |
| Polymer Film In | 1478 | 176 | 367.0 | 1.021 | 1.42 |
| Laminate Out | | 176 | 364.3 | 1.02 | 7.71 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web comprising:
   a. a polymeric film layer comprising a film surface existing in a plane;
   b. a fibrous layer adjacent the polymeric film layer; and
   c. a plurality of film sections that are partially torn away from the polymeric film layer to define tunnel-shaped caps that extend to a position above the plane of the film surface, the tunnel-shaped caps including a first opening located at one of its longitudinal ends, an opposing second opening located at the other of its longitudinal ends, and a cap length extending between the first opening and the second opening;
   d. wherein at least some of the caps comprises a third opening along the cap length, and
   e. wherein fibers from the fibrous layer extend above the plane of the film surface and are at least partially covered by individual caps.

2. The web of claim 1, wherein the polymeric film comprises microbubbles.

3. The web of claim 1, wherein the polymeric film comprises micro apertures.

4. The web of claim 1, wherein the polymeric film is hydrophobic.

5. A web comprising:
   a. a polymeric film layer comprising a film surface existing in a plane; and
   b. a plurality of film sections that are partially torn away from the polymeric film layer to define tunnel-shaped caps that extend to a position above the plane of the film surface, the tunnel-shaped caps including a first opening located at one of its longitudinal ends, an opposing second opening located at the other of its longitudinal ends, and a cap length extending between the first opening and the second opening;

c. wherein at least some of the caps comprises a third opening along the cap length, and
d. wherein a distal portion of the caps has a thickness which is less than that of the polymeric film at the film surface.

* * * * *